(12) United States Patent
Cook et al.

(10) Patent No.: US 12,415,779 B2
(45) Date of Patent: Sep. 16, 2025

(54) PROCESSES OF MAKING 3-FLUORO-5-(((1S,2AR)-1,3,3,4,4-PENTAFLUORO-2A-HYDROXY-2,2A,3,4-TETRAHYDRO-1H-CYCLOPENTA[CD]INDEN-7-YL)OXY)-BENZONITRILE AND POLYMORPHS THEREOF

(71) Applicant: NiKang Therapeutics, Inc., Wilmington, DE (US)

(72) Inventors: Charles M. Cook, Wilmington, DE (US); Jiping Fu, Danville, CA (US); Yigang He, Newark, DE (US); Yan Lou, Pleasanton, CA (US); Rongzhen Chen, Jiangsu (CN); Yan Dong, Jiangsu (CN)

(73) Assignee: NIKANG THERAPEUTICS, INC., Wilmington, DE (US)

( * ) Notice: Subject to any disclaimer, the term of this patent is extended or adjusted under 35 U.S.C. 154(b) by 87 days.

(21) Appl. No.: 17/963,926

(22) Filed: Oct. 11, 2022

(65) Prior Publication Data
US 2023/0115881 A1  Apr. 13, 2023

(30) Foreign Application Priority Data
Oct. 12, 2021 (WO) ................ PCT/CN2021/123248
Oct. 13, 2021 (WO) ................ PCT/CN2021/123407

(51) Int. Cl.
*A61K 9/20*   (2006.01)
*A61K 9/00*   (2006.01)
(Continued)

(52) U.S. Cl.
CPC .......... *C07C 255/54* (2013.01); *A61K 9/0019* (2013.01); *A61K 9/0043* (2013.01); *A61K 9/0048* (2013.01); *A61K 9/0078* (2013.01); *A61K 9/06* (2013.01); *A61K 9/08* (2013.01); *A61K 9/2013* (2013.01); *A61K 9/2018* (2013.01); *A61K 9/2054* (2013.01); *A61K 9/2059* (2013.01); *A61K 9/4825* (2013.01); *A61K 9/4858* (2013.01); *A61K 47/10* (2013.01);
(Continued)

(58) Field of Classification Search
None
See application file for complete search history.

(56) References Cited

U.S. PATENT DOCUMENTS 11,267,782 B2   3/2022   Fu et al.
11,420,936 B2   8/2022   Fu et al.
(Continued)

FOREIGN PATENT DOCUMENTS

WO   WO 2020/081695 A1   4/2020
WO   WO 2020/214853 A1   10/2020
(Continued)

OTHER PUBLICATIONS

International Search Report and Written opinion of PCT/CN2021/123248 dated Jul. 8, 2022; 16 pages.
(Continued)

*Primary Examiner* — Adam C Milligan
*Assistant Examiner* — Jason Nolan
(74) *Attorney, Agent, or Firm* — Squire Patton Boggs (US) LLP

(57) ABSTRACT

The present disclosure provides certain processes of making 3-fluoro-5-(((1S,2aR)-1,3,3,4,4-pentafluoro-2a-hydroxy-2,2a,3,4-tetrahydro-1H-cyclopenta[cd]inden-7-yl)oxy)-benzonitrile (Compound 1) and certain polymorphs thereof. Also provided are pharmaceutical compositions comprising a crystalline polymorph form of Compound 1 and processes for preparing such polymorph forms.

34 Claims, 4 Drawing Sheets

XRPD of DEA Solvate of Compound 1

(51) Int. Cl.

| | | |
|---|---|---|
| | *A61K 9/06* | (2006.01) |
| | *A61K 9/08* | (2006.01) |
| | *A61K 9/48* | (2006.01) |
| | *A61K 47/10* | (2017.01) |
| | *A61K 47/12* | (2006.01) |
| | *A61K 47/14* | (2017.01) |
| | *A61K 47/26* | (2006.01) |
| | *A61K 47/38* | (2006.01) |
| | *C07C 253/30* | (2006.01) |
| | *C07C 253/34* | (2006.01) |
| | *C07C 255/54* | (2006.01) |

(52) U.S. Cl.
CPC .............. *A61K 47/12* (2013.01); *A61K 47/14* (2013.01); *A61K 47/26* (2013.01); *A61K 47/38* (2013.01); *C07C 253/30* (2013.01); *C07C 253/34* (2013.01); *C07B 2200/13* (2013.01)

(56) References Cited

U.S. PATENT DOCUMENTS

| | | |
|---|---|---|
| 11,634,382 B2 | 4/2023 | Fu et al. |
| 11,753,366 B2 | 9/2023 | Fu et al. |
| 2021/0380536 A1 | 12/2021 | Fu et al. |
| 2022/0274914 A1 | 9/2022 | Fu et al. |
| 2022/0380302 A1 | 12/2022 | Fu et al. |
| 2023/0202970 A1 | 6/2023 | Fu et al. |
| 2023/0373909 A1 | 11/2023 | Fu et al. |

FOREIGN PATENT DOCUMENTS

| | | |
|---|---|---|
| WO | WO 2021/016280 A1 | 1/2021 |
| WO | WO 2021/212062 A1 | 10/2021 |
| WO | WO 2022/082329 A1 | 4/2022 |
| WO | WO 2022/086822 A1 | 4/2022 |
| WO | WO 2023/076532 A1 | 5/2023 |

OTHER PUBLICATIONS

International Search Report and Written opinion of PCT/CN2021/123407 dated Nov. 3, 2022; 17 pages.

Barnett et al. The mechanism and an Improved Asymmetric Allylboration of Ketones Catalyzed by Chiral Biphenols Angewandte Chemie International Edition, 2009, 48, 8679-8682.

Pirnot et al. "Manufacturing Process Development for Belzutifan, Part 6: Ensuring Scalability for a Deoxyfluorination Reaction" Organic Process Research and Development, 2022, 26, 551-559.

Yin et al. "Direct and Convenient Conversion of Alcohols to Fluorides" Organic Letters, 2004, 6, 1465-1468.

International Preliminary Report on Patentability of PCT/US2022/046323 dated Apr. 25, 2024; 9 pages.

International Search Report and Written opinion of PCT/US2022/046323 dated Apr. 6, 2023; 14 pages.

PROCESSES OF MAKING 3-FLUORO-5-(((1S,2AR)-1,3,3,4,4-PENTAFLUORO-2A-HYDROXY-2,2A,3,4-TETRAHYDRO-1H-CYCLOPENTA[CD]INDEN-7-YL)OXY)-BENZONITRILE AND POLYMORPHS THEREOF

CROSS-REFERENCE TO RELATED APPLICATIONS

The application is a U.S. Nonprovisional application claiming the benefit of International Application PCT/CN2021/123248, filed Oct. 12, 2021, and PCT/CN2021/123407, filed on Oct. 13, 2021, the entire contents of each of which are hereby incorporated by reference in their entireties.

FIELD OF THE DISCLOSURE

The present disclosure provides certain processes of making 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile according to the following structure:

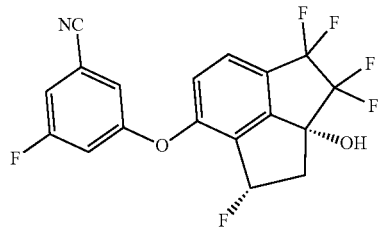 [SMILES: N#Cc1cc(F)cc(Oc2ccc3c4c2[C@@H](F)C[C@]4(O)C(F)(F)C3(F)F)c1]

and referred to herein as ("Compound 1") and certain polymorphs thereof. Also provided are pharmaceutical compositions comprising a crystalline polymorph form of Compound 1 and processes for preparing such polymorph forms.

BACKGROUND

Compound 1 is a hypoxia inducible factor-2α (HIF-2α) inhibitor and is being developed for treating various diseases, including cancer, such as renal cancer, glioblastoma, neuroblastoma, pheochromocytomas, paragangliomas, somatostatinomas, hemangioblastomas, gastrointestinal stromal tumors (GIST), pituitary tumors, leiomyomas, leiomyosarcomas, polycythaemia, and retinal tumors, and non-cancer diseases such as pulmonary artery hypertension (PAH), reflux esophagitis, hepatic steatosis, NASH, inflammatory disease (such as inflammatory bowel disease), autoimmune disease (such as Graft-versus-Host-Disease), and iron overload.

Compound 1 is disclosed in Table 1, as compound No. 5, of PCT Application No. Publication No. WO 2020/214853. The published processes for making Compound 1 generates impurities, requiring purification of Compound 1 by column chromatography. From a cost and operational standpoint, use of column chromatography for large scale manufacture of drug substance is unsuitable. Therefore, there is a need to identify a scalable process that can produce Compound 1 that meets regulatory and other purity requirements and is cost effective on large scale, including commercial scale.

The polymorphic behavior of small molecule drugs can be critical in pharmacology since the same small molecule can have different physical properties as a result of the arrangement of molecules in the crystal lattice. These different properties can affect pharmaceutical parameters such as storage stability, compressibility, density, hygroscopy, dissolution rates, and bioavailability. It is known that one polymorph can convert into another polymorph, and in some cases this happens spontaneously. Accordingly, there is a need to find a thermodynamically stable polymorph of a small molecule drug. The present disclosure fulfills these and related needs.

SUMMARY

Among the various aspects of the present disclosure may be noted the provision of a process for the synthesis of Compound 1 that is suitable for large scale synthesis of Compound 1 in a cost-effective manner. The process is based, in part, on the discovery by Applicant that Compound 1 can form amine solvates with certain organic amines. Formation of such amine solvates by Compound 1 enables removal of certain impurities generated in the synthesis of Compound 1, to provide Compound 1 in high purity without the need for column chromatography.

In a first aspect, provided is a crystalline form of Compound 1, designated as Form A polymorph, having an X-ray powder diffraction pattern comprising peaks at angular positions 15.8 and 18.6, wherein the angular positions may vary by ±0.2° 2θ as measured by X-ray powder diffraction at ambient temperature using (Cu Kα) an X-ray wavelength of 1.5418 Å. In an embodiment of the first aspect, the X-ray powder diffraction is determined at about 23° C. to about 25° C.

In a second aspect, provided is an amine solvate of Compound 1, wherein the amine is:
(i) $NHR^1R^2$ where (1) $R^1$ is hydrogen and $R^2$ is $C_2$-$C_{12}$ alkyl, $C_2$-$C_6$ alkenyl, $C_2$-$C_6$ alkynyl, $C_3$-$C_7$ cycloalkyl, or $C_3$-$C_7$ cycloalkyl-$C_{1-6}$ alkyl; (2) $R^1$ is $C_1$-$C_6$ alkyl, $C_2$-$C_6$ alkenyl, $C_2$-$C_6$ alkynyl, $C_3$-$C_7$ cycloalkyl, or $C_3$-$C_7$ cycloalkyl-$C_{1-6}$ alkyl and $R^2$ is $C_1$-$C_6$ alkyl, $C_2$-$C_6$ alkenyl, $C_2$-$C_6$ alkynyl, $C_3$-$C_7$ cycloalkyl, or $C_3$-$C_7$ cycloalkyl-$C_{1-6}$ alkyl; or (3) $R^1$ and $R^2$ together with the nitrogen atom to which they are attached form cyclylamine; or
(ii) $R^3R^4N$—$(CH_2)_n$—$NR^5R^6$ where n is an integer selected from 1 to 6 and $R^3$, $R^4$, $R^5$, and $R^6$ are independently H, $C_1$-$C_6$ alkyl, or $C_3$-$C_7$ cycloalkyl.

In a third aspect, provided is a crystalline form of a diethylamine solvate of Compound 1, designated as Form B polymorph, having an X-ray powder diffraction pattern comprising peaks at angular positions 13.8 and 21.3, wherein the angular positions may vary by ±0.2° 2θ as measured by X-ray powder diffraction at ambient temperature using (Cu Kα) an X-ray wavelength of 1.5406 Å. In an embodiment of the third aspect, the X-ray powder diffraction is determined at about 23° C. to about 25° C.

In a fourth aspect, provided is a process of preparing an amine solvate of Compound 1, wherein the amine is:
(i) $NHR^1R^2$ where (1) $R^1$ is hydrogen and $R^2$ is $C_2$-$C_{12}$ alkyl, $C_2$-$C_6$ alkenyl, $C_2$-$C_6$ alkynyl, $C_3$-$C_7$ cycloalkyl, or $C_3$-$C_7$ cycloalkyl-$C_{1-6}$ alkyl; (2) $R^1$ is $C_1$-$C_6$ alkyl, $C_2$-$C_6$ alkenyl, $C_2$-$C_6$ alkynyl, $C_3$-$C_7$ cycloalkyl, or $C_3$-$C_7$ cycloalkyl-$C_{1-6}$ alkyl and $R^2$ is $C_1$-$C_6$ alkyl, $C_2$-$C_6$ alkenyl, $C_2$-$C_6$ alkynyl, $C_3$-$C_7$ cycloalkyl, or $C_3$-$C_7$ cycloalkyl-$C_{1-6}$ alkyl; or (3) $R^1$ and $R^2$ together with the nitrogen atom to which they are attached form cyclylamine; or
(ii) $R^3R^4N$—$(CH_2)_n$—$NR^5R^6$ where n is an integer selected from 1 to 6 and $R^3$, $R^4$, $R^5$, and $R^6$ are independently H, $C_1$-$C_6$ alkyl or $C_3$-$C_7$ cycloalkyl, comprising:

(a1) contacting Compound 1 with the amine NHR$^1$R$^2$ or R$^3$R$^4$—N—(CH$_2$)$_n$—R$^5$R$^6$ where R$^1$, R$^2$, R$^3$, R$^4$, R$^5$, and R$^6$, and n are as defined in (i) and (ii), respectively, in the presence or absence of one or more suitable organic solvents;

(b1) optionally adding (i) one or more anti-solvents and/or (ii) a solid crystalline seed of Compound 1, or a solid crystalline seed of the amine solvate of Compound 1, or a combination thereof, to the mixture of Step (a1) to precipitate the amine solvate of Compound 1;

(c1) isolating the solid of Step (b1) to obtain a solid amine solvate of Compound 1; and (d1) optionally converting the amine solvate of Compound 1 from any one of Steps (a1) to (c1) to Compound 1.

Provided is the process of the fourth aspect, further comprising preparing the Compound 1 of Step (a1), comprising:

(a) treating 3-fluoro-5-(((1R,2aR)-3,3,4,4-tetrafluoro-1,2a-dihydroxy-2,2a,3,4-tetrahydro-1H-cyclopenta[cd]inden-7-yl)oxy)benzonitrile with a deoxyfluorinating agent, with or without a base, in a suitable organic solvent and optionally in the presence of triethylamine trihydrofluoride (Et$_3$N·3HF); and (b) purifying the mixture from Step (a) to obtain Compound 1.

In a fifth aspect, provided is a process of preparing crystalline Form B polymorph of a diethylamine solvate of Compound 1 as described in Embodiments C1 to C9 (disclosed herein below), comprising:

(a2) contacting 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile (Compound 1) with diethylamine, in the presence or absence of one or more suitable organic solvents;

(b2) optionally adding (i) one or more anti-solvents and/or (ii) a crystalline seed of Compound 1, or a solid crystalline seed of the amine solvate of Compound 1, or a combination thereof, to the mixture of Step (a2) to precipitate crystalline Form B polymorph of the diethylamine solvate of Compound 1; and (c2) isolating the crystalline Form B polymorph of the diethylamine solvate of Compound 1; and (d2) optionally converting the crystalline Form B polymorph of the diethylamine solvate of Compound 1 from Step (c2) to Compound 1.

In a sixth aspect, provided is a process of preparing crystalline Form A polymorph of Compound 1 (as defined in Embodiment A1 to A11 herein below), from diethylamine solvate of Compound 1, comprising:

(a3) removing diethylamine from the diethylamine solvate of Compound 1; and (b3) optionally recrystallizing crystalline Form A polymorph of Compound 1 obtained from Step (a3).

In a seventh aspect, provided is a process of making crystalline Form A polymorph of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile (Compound 1), comprising:

(a4) contacting a solution of Compound 1 in one or more suitable organic solvents with one or more anti-solvents;

(b4) optionally adding a solid crystalline seed of Compound 1; and (c4) isolating the crystalline Form A polymorph of Compound 1 from the mixture.

In an eighth aspect, provided is a process for making Compound 1 from 3-fluoro-5-(((1R,2aR)-3,3,4,4-tetrafluoro-1,2a-dihydroxy-2,2a,3,4-tetrahydro-1H-cyclopenta[cd]inden-7-yl)oxy)benzonitrile comprising:

(a5) treating 3-fluoro-5-(((1R,2aR)-3,3,4,4-tetrafluoro-1,2a-dihydroxy-2,2a,3,4-tetrahydro-1H-cyclopenta[cd]inden-7-yl)oxy)benzonitrile with perfluorobutanesulfonyl fluoride (PBSF) and Et$_3$N·3HF in the presence of an organic base, in one or more suitable organic solvents;

(b5) purifying the mixture from Step (a5) to obtain Compound 1;

(c5) optionally converting Compound 1 from Step (b5) to an amine solvate of the second aspect or any embodiments thereof disclosed herein below; and (d5) optionally converting the amine solvate of Compound 1 obtained from Step (c5) to crystalline Form A polymorph of Compound 1 as disclosed in the first aspect or any embodiments thereof disclosed herein below.

In a ninth aspect, provided is a solid composition comprising a diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile and 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile, wherein the % weight ratio of the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile ("DEA solvate of Compound 1") to 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile (Compound 1) in the composition is about 1 part DEA solvate to 9 or fewer parts Compound 1. In an embodiment of the ninth aspect, provided is a solid composition comprising a diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile and 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile, wherein the % weight ratio of the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile to 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile in the composition is from about 1:9 to about 1:0.001.

In a tenth aspect, provided is a method of treating a disease treatable by inhibition of HIF-2α in a patient, preferably the patient is in need of such treatment, which method comprises administering to the patient, preferably a patient in need of such treatment, a therapeutically effective amount of crystalline Form A polymorph of Compound 1 as defined in the first aspect above or any one of embodiments thereof disclosed herein in a pharmaceutical composition comprising a pharmaceutically acceptable excipient.

In one embodiment of the tenth aspect, the disease is cancer, such as renal cancer, clear cell renal cell carcinoma, liver cancer, hepatocellular carcinoma (HCC), pancreatic cancer, pancreatic neuroendocrine tumor, gastric cancer, ovarian cancer, non-small cell lung cancer, colorectal cancer (CRC), pancreatic ductal adenocarcinoma (PDAC), biliary tract cancer (BTC), glioblastoma (see PNAS 2017, 114, E6137-E6146), neuroblastoma, pheochromocytomas and paragangliomas (see European Journal of Cancer 2017, 86, 1-4), somatostatinomas, hemangioblastomas, gastrointestinal stromal tumors (GIST), pituitary tumors, leiomyomas, leiomyosarcomas, polycythaemia, retinal tumors, cancers with one or more EPAS1/HIF2A mutations such as uterine cancer, pheochromocytoma/paraganglioma, melanoma, stomach cancer, lung adenocarcinoma, esophagus cancer, lung squamous cancer, ovarian cancer, cervical cancer, head & neck cancer, liver cancer, colorectal cancer, breast cancer, renal cell carcinoma, diffuse large B-cell lymphoma, glioblastoma, thymoma, prostate cancer, pancreatic cancer, sarcoma, and low-grade gliomas, and cancers with one or more ELOC/TCEB1 mutations such as prostate cancer, uterine cancer, liver cancer, breast cancer, pancreatic cancer, ovarian cancer, lung adenocarcinoma, head and neck cancer, stomach cancer, sarcoma, colorectal cancer, lung squamous cancer, esophagus cancer, diffuse large B-cell lymphoma, melanoma, renal cell carcinoma, cervical cancer, pheochromocytoma/paraganglioma, adenoid cystic carcinoma, acute myeloid leukemia, glioblastoma, and low-grade gliomas.

In another embodiment, non-cancer diseases that could benefit from Hif-2α inhibition include VHL (von Hippel-Lindau) disease (see Oncotarget, 2015, 6, 23036-23037), PAH (pulmonary artery hypertension) (see Mol. Cell. Biol. 2016, 36, 1584-1594), esophagitis, reflux esophagitis (see Current Opinion in Pharmacology 2017, 37: 93-99), hepatic steatosis (see Nature Medicine 2017, 23, 1298-1308), NASH, inflammatory disease such as inflammatory bowel disease (see Nature Reviews gastroenterology & Hepatology 2017, 14, 596), autoimmune disease such as Graft-versus-Host-Disease (see Blood, 2015, 126, 1865), and iron overload.

In an eleventh aspect, provided is a pharmaceutical composition comprising crystalline Form A polymorph of Compound 1 as defined in the first aspect above or any one of embodiments thereof disclosed herein; and a pharmaceutically acceptable excipient.

In a twelfth aspect, provided is a pharmaceutical composition prepared with crystalline Form A polymorph of Compound 1 as defined in the first aspect above or any one of embodiments thereof disclosed herein; and a pharmaceutically acceptable excipient.

In a thirteenth aspect. provided is a method of inhibiting HIF2α which method comprises contacting HIF2α with crystalline Form A polymorph of Compound 1 as defined in the first aspect above or any one of embodiments thereof disclosed herein; or contacting HIF2α with a pharmaceutical composition comprising crystalline Form A polymorph of Compound 1 as defined in the first aspect above or any one of embodiments thereof disclosed herein, and a pharmaceutically acceptable excipient.

In a fourteenth aspect, provided is crystalline Form A polymorph of Compound 1 as defined in the first aspect above or any one of embodiments thereof disclosed herein for use in the treatment of a disease mediated by HIF-2α. In an embodiment of the fourteenth aspect, the disease are those disclosed herein including those disclosed in the first embodiment of the tenth aspect.

In any of the aforementioned aspects involving the treatment of cancer, provided are further embodiments comprising administering crystalline Form A polymorph of Compound 1 as defined in the first aspect above or any one of embodiments thereof, in combination with at least one additional anticancer agent such as an EGFR inhibitor gefitinib, erlotinib, afatinib, icotinib, neratnib, rociletinib, cetuximab, panitumumab, zalutumumab, nimotuzumab, or matuzumab. In another embodiment, the crystalline Form A polymorph of Compound 1 as defined in the first aspect above or any one of embodiments thereof, is administered in combination with a HER2/neu inhibitor including lapatinib, trastuzumab, and pertuzumab. In another embodiment, the crystalline Form A polymorph of Compound 1 as defined in the first aspect above or any one of embodiments thereof, is administered in combination with a PI3k/mTOR inhibitor including idelalisib, buparlisib, BYL719, and LY3023414. In another embodiment, the crystalline Form A polymorph of Compound 1 as defined in the first aspect above or any one of embodiments thereof, is administered in combination with a VEGF inhibitor such as bevacizumab, and/or a multi-tyrosine kinase inhibitors such as sorafenib, sunitinib, pazopanib, and cabozantinib. In another embodiment, the crystalline Form A polymorph of Compound 1 as defined in the first aspect above or any one of embodiments thereof, is administered in combination with an immunotherapeutic agents such as PD-1 and PD-L1 inhibitors, CTLA4 inhibitors, IDO inhibitors, TDO inhibitors, A2A agonists, A2B agonists, STING agonists, RIG-1 agonists, Tyro/Axl/Mer inhibitors, glutaminase inhibitors, arginase inhibitors, CD73 inhibitors, CD39 inhibitors, TGF-β inhibitors, IL-2, interferon, PI3K-γ inhibitors, CSF-1R inhibitors, GITR agonists, OX40 agonists, TIM-3 antagonists, LAG-3 antagonists, CAR-T therapies, and therapeutic vaccines. When combination therapy is used, the agents can be administered simultaneously or sequentially.

DETAILED DESCRIPTION

Definitions

Figure 1:
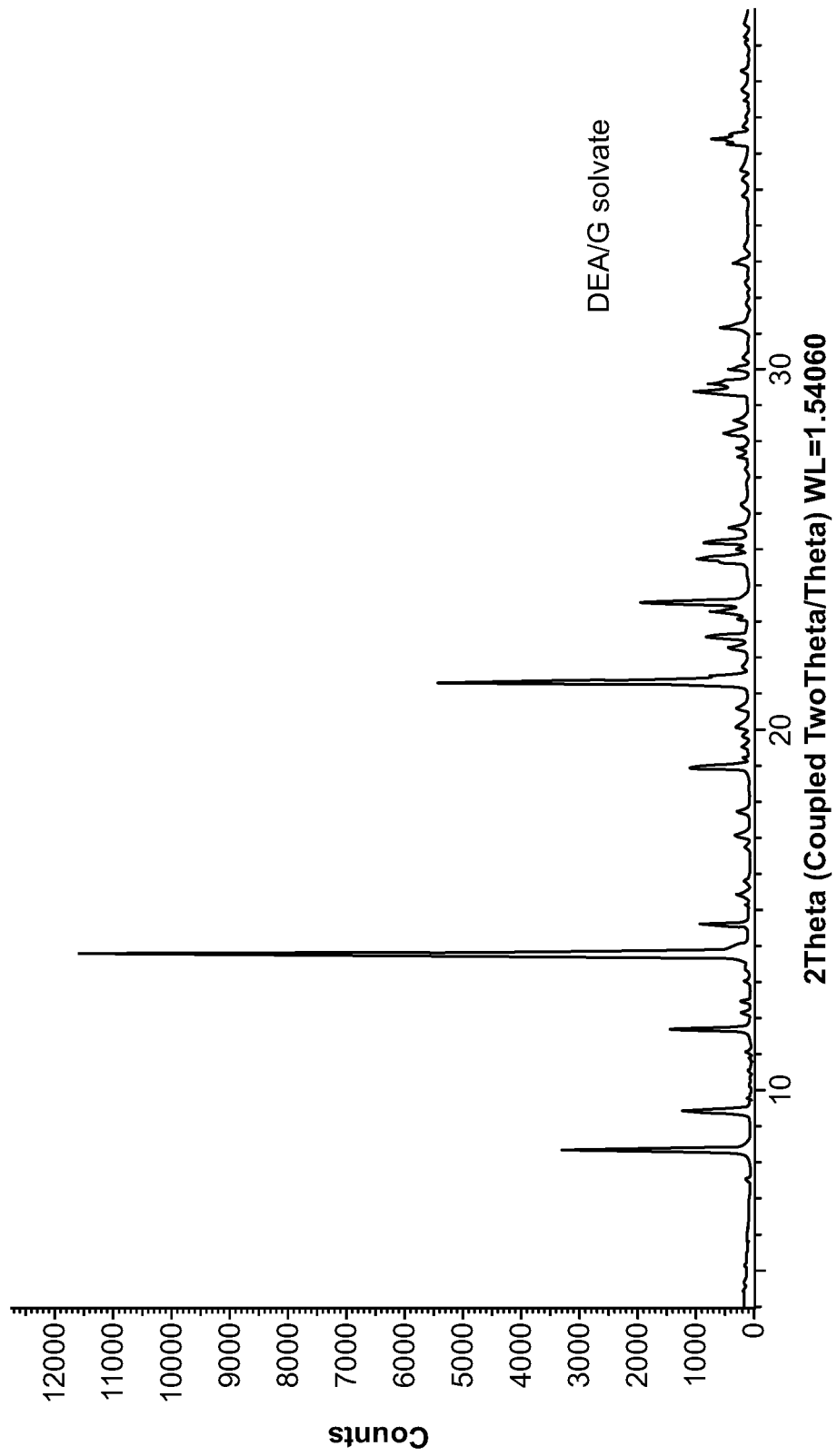
FIG. 1 depicts a representative XRPD diffractogram of crystalline Form B polymorph of a diethylamine (DEA) solvate of Compound 1, prepared according to the method described in Example 4.
Figure 2:
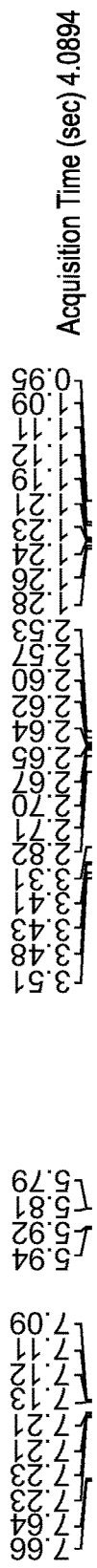
FIG. 2 depicts a representative $^1$HNMR spectrum of a diethylamine solvate of Compound 1, prepared according to the method described in Example 4.
Figure 2:
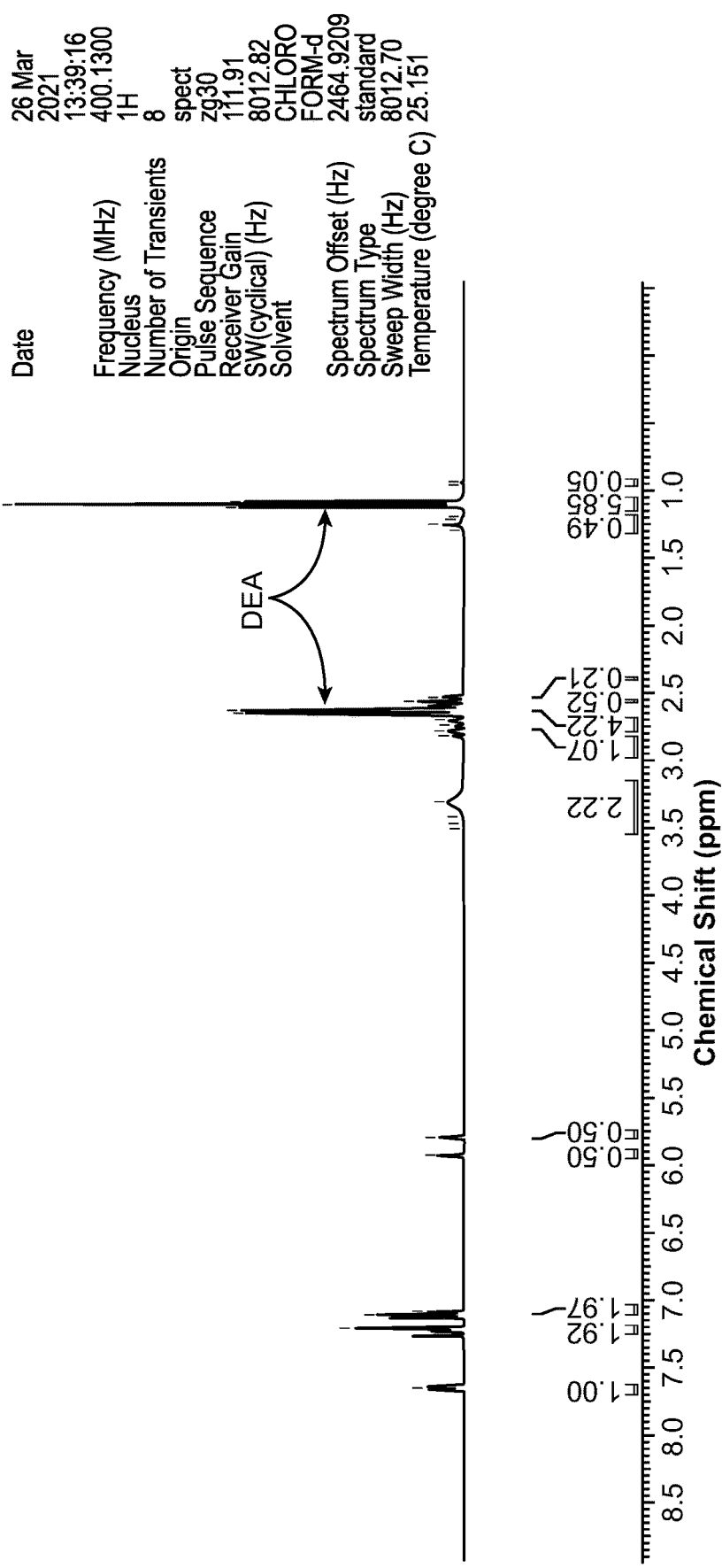

Unless otherwise stated, the following terms used in the specification and claims are defined for the purposes of this Application and have the following meaning:

"Alkyl" means a linear or branched saturated monovalent hydrocarbon radical of one to six carbon atoms i.e., $C_1$-$C_6$ alkyl, unless stated otherwise e.g., $C_2$-$C_{12}$ alkyl means an alkyl radical (i.e., linear or branched saturated monovalent hydrocarbon radical) as defined above that contains 2 to 12 carbon atoms. Examples include, but are not limited to, methyl, ethyl, propyl, 2-propyl, butyl, pentyl, and the like.

"$C_1$-$C_6$ alkylene" means a linear or branched saturated divalent hydrocarbon radical of one to six carbon atoms. Examples include, but are not limited to, methylene, —CH$_2$CH$_2$—, —CH$_2$CH$_2$CH$_2$—, —CH$_2$CH(CH$_3$)—, —CH$_2$CH$_2$CH$_2$CH$_2$— (and isomers thereof), —CH$_2$CH$_2$CH$_2$CH$_2$CH$_2$— (and isomers thereof), and the like.

"$C_2$-$C_6$ alkenyl" means a linear or branched monovalent hydrocarbon radical of two to six carbon atoms containing a single double bond. Examples include, but are not limited to, vinyl, allyl, and the like.

"C$_2$-C$_6$ alkynyl" means a linear or branched monovalent hydrocarbon radical of two to six carbon atoms containing a single triple bond. Examples include, but are not limited to, ethynyl, propargyl, and the like.

"C$_3$-C$_7$ cycloalkyl" means a monocyclic saturated monovalent hydrocarbon radical of three to seven carbon atoms optionally substituted with one or two alkyl. Examples include, but are not limited to, cyclopropyl, cyclobutyl, cyclopentyl, cyclohexyl, and the like.

"C$_3$-C$_7$ cycloalkyl-C$_{1-6}$ alkyl" means a —C$_{1-6}$ alkylene-R group where C$_{1-6}$ alkylene is as defined above and R is C$_3$-C$_7$ cycloalkyl as defined above. Examples include, but are not limited to, cyclopropylmethyl, cyclobutylmethyl, cyclopentylethyl, cyclohexylmethyl, and the like.

"Cyclylamine" means a saturated monocyclic ring of 4 to 8 ring atoms in which one ring atom is nitrogen and an additional ring atom can be a heteroatom independently selected from N, O, and S(O)$_n$, where n is an integer selected from 0 to 2, the remaining ring atoms being C. The cyclylamine may be substituted with one or two alkyl as defined herein. Representative examples include, but is not limited to, pyrrolidine, piperidine, homopiperidine, morpholine, piperazine, thiomorpholine, and the like.

The term "solvate" refers to forms of a compound where the compound is associated by a non-covalent bond to a solvent molecule. This physical association may include hydrogen bonding. As used herein, an amine solvate of Compound 1 refers to forms of Compound 1 that are associated with an amine NHR$^1$R$^2$ or R$^3$R$^4$N—(CH$_2$)$_n$—NR$^5$R$^6$, each as defined herein and includes both stoichiometric solvates and non-stoichiometric solvates. In certain instances, the amine solvate of Compound 1 are isolable, for example, when an amine molecule is incorporated in the crystal lattice of a crystalline solid of Compound 1. In certain instances, the amine solvate of Compound 1 are present in situ. An amine solvate of Compound 1 thus includes both isolable and in situ solvates. An amine solvate of Compound 1 present in situ are also referred to herein as adducts.

The present disclosure includes a polymorphic form of Compound 1 and diethylamine solvate of Compound 1. Polymorphs are crystalline forms of a compound that differ in arrangements of the molecules of that compound in a crystal lattice. Therefore, a single compound may give rise to a variety of polymorphic forms. The polymorphs of a compound usually have different melting points, solubilities, densities, and optical properties. Polymorphic forms of a compound can be distinguished by a number of techniques well known in the art such as X-ray diffractometry, IR, or Raman spectroscopy.

"XRPD" means X-ray powder diffraction, an analytical technique which measures the diffraction of X-rays in the presence of a solid component. Materials which are crystalline and have regular repeating arrays of atoms generate a distinctive powder pattern.

"Substantially free" as used herein refers to crystalline Form A polymorph of Compound 1 (i.e. 3-fluoro-5-(((1S, 2aR)-1,3,3,4,4-pentafluoro-2a-hydroxy-2,2a,3,4-tetrahydro-1H-cyclopenta[cd]inden-7-yl)oxy)benzonitrile) that has less than about 10% by weight of 3-fluoro-5-(((1R,2aS)-1,3,3,4,4-pentafluoro-2a-hydroxy-2,2a,3,4-tetrahydro-1H-cyclopenta[cd]inden-7-yl)oxy)benzonitrile enantiomer of Compound 1 (hereinafter the "(1R,2aS) enantiomer"). In one embodiment, crystalline Form A polymorph of Compound 1 has less than about 8% by weight the (1R,2aS) enantiomer. In another embodiment, crystalline Form A polymorph of Compound 1 has less than about 7% by weight the (1R,2aS) enantiomer. In yet another embodiment, crystalline Form A polymorph of Compound 1 has less than about 6% by weight the (1R,2aS) enantiomer. In yet another embodiment, crystalline Form A polymorph of Compound 1 has less than about 5% by weight the (1R,2aS) enantiomer. In yet another embodiment, crystalline Form A polymorph of Compound 1 has less than about 4% by weight the (1R,2aS) enantiomer. In yet another embodiment, crystalline Form A polymorph of Compound 1 has less than about 3% by weight the (1R,2aS) enantiomer. In yet another crystalline Form A polymorph of Compound 1 has less than about 2% by weight the (1R,2aS) enantiomer. In yet another embodiment, crystalline Form A polymorph of Compound 1 has less than about 1% by weight the (1R,2aS) enantiomer. In yet another embodiment, crystalline Form A polymorph of Compound 1 has less than about 0.8% by weight the (1R,2aS) enantiomer. In yet another embodiment, crystalline Form A polymorph of Compound 1 has less than about 0.7% by weight the (1R,2aS) enantiomer. In yet another embodiment, crystalline Form A polymorph of Compound 1 has less than about 0.6% by weight the (1R,2aS) enantiomer. In yet another embodiment, crystalline Form A polymorph of Compound 1 has less than about 0.5% by weight the (1R,2aS) enantiomer. In yet another embodiment, crystalline Form A polymorph of Compound 1 has less than about 0.4% by weight the (1R,2aS) enantiomer. In yet another embodiment, crystalline Form A polymorph of Compound 1 has less than about 0.3% by weight the (1R,2aS) enantiomer. In yet another embodiment, crystalline Form A polymorph of Compound 1 has less than about 0.2% by weight the (1R,2aS) enantiomer. In yet another embodiment, crystalline Form A polymorph of Compound 1 has less than about 0.1% by weight the (1R,2aS) enantiomer. In yet another embodiment, crystalline Form A polymorph of Compound 1 has less than about 0.05% by weight the (1R,2aS) enantiomer.

"Substantially pure" as used herein refers to a solid-state form of Compound 1 that contain less than about 5% by weight total impurities or less than about 5% of total impurities as measured by HPLC. The phrase "crystalline Form A polymorph is substantially pure" means that Form A polymorph of Compound 1 that contain less than about 5% by weight total impurities or less than about 5% of total impurities as measured by HPLC. In one embodiment, crystalline Form A polymorph of Compound 1 that contain less than about 4% by weight total impurities or less than about 4% of total impurities as measured by HPLC. In another embodiment, crystalline Form A polymorph of Compound 1 that contain less than about 3% by weight total impurities or less than about 5% of total impurities as measured by HPLC. In yet another embodiment, crystalline Form A polymorph of Compound 1 that contain less than about 2% by weight total impurities or less than about 2% of total impurities as measured by HPLC. In yet another embodiment, crystalline Form A polymorph of Compound 1 that contain less than about 1% by weight total impurities or less than about 1% of total impurities as measured by HPLC. In yet another embodiment, crystalline Form A polymorph of Compound 1 that contain less than about 0.9% by weight total impurities or less than about 0.9% of total impurities as measured by HPLC. In yet another embodiment, crystalline Form A polymorph of Compound 1 that contain less than about 0.8% by weight total impurities or less than about 0.8% of total impurities as measured by HPLC. In yet another embodiment, crystalline Form A polymorph of Compound 1 that contain less than about 0.7% by weight total impurities or less than about 0.7% of total impurities as measured by HPLC. In yet another embodiment, crystalline Form A polymorph of Compound 1 that contain less than about 0.6% by weight total impurities or less than about 0.6% of total impurities as measured by HPLC. In yet another embodiment, crystalline Form A polymorph of Compound 1 that contain less than about 0.5% by weight total impurities or less than about 0.5% of total impurities as measured by HPLC. In yet another embodiment, crystalline Form A polymorph of Compound 1 that contain less than about 0.4% by weight total impurities or less than about 0.4% of total impurities as measured by HPLC. In yet another embodiment, crystalline Form A polymorph of Compound 1 that contain less than about 0.3% by weight total impurities or less than about 0.3% of total impurities as measured by HPLC. In yet another embodiment, crystalline Form A polymorph of Compound 1 that contain less than about 0.2% by weight total impurities or less than about 0.2% of total impurities as measured by HPLC. In yet another embodiment, crystalline Form A polymorph of Compound 1 that contain less than about 0.1% by weight total impurities or less than about 0.1% of total impurities as measured by HPLC. Impurities include, but are not limited to, synthesis by-products, residual starting materials, reagents, residual organic solvent, and the like.

"Substantially identical" as used herein refers to measured physical characteristics that are comparable in value or data traces that are comparable in peak position and amplitude or intensity within the scope of variations that are typically associated with sample positioning or handling or the identity of the instrument employed to acquire the traces or physical characteristics or due to other variations or fluctuations normally encountered within or between laboratory environments or analytical instrumentation.

As used herein, the term "reacting", "treating" or "contacting" when describing a certain process is used as known in the art and generally refers to the bringing together of chemical reagents in such a manner so as to allow their interaction at the molecular level to achieve a chemical or physical transformation. The "reacting", "treating" or "contacting" steps of the processes described herein can be conducted for a time and under conditions suitable for preparing the identified product.

"Anti-solvent" as used herein means a solvent in which Compound 1 or diethylamine solvate of Compound 1 is less soluble. In one embodiment, an antisolvent is a solvent in which Compound 1 is less soluble. In another embodiment, an antisolvent is a solvent in which Compound 1 has a solubility of less than about 50 mg/mL. In yet another embodiment, an antisolvent is a solvent in which Compound 1 an antisolvent is a solvent in which Compound 1 has a solubility of less than about 25 mg/mL.

"Suitable organic solvent" or "first suitable organic solvent" refers to an organic solvent which, under the reaction conditions of the processes disclosed herein, does not enter into any appreciable reaction with either the reactants, intermediates and/or the products at the temperatures at which the reactions are carried out. A given reaction disclosed herein can be carried out in one organic solvent or a mixture of two or more organic solvents. Examples of suitable organic solvents that can be used in the reactions described herein include polar (protic and/or aprotic) and nonpolar organic solvents e.g., halogenated alkanes such as carbon tetrachloride, chloroform, dichloromethane, 1,2-dichloroethane, and the like; ethers such as tetrahydrofuran, 2-methyltetrahydrofuran, 1,3-dioxane, 1,4-dioxane, diethyl ether, diisopropyl ether, methyl t-butyl ether, and the like; alcohols such as methanol, ethanol, 1-propanol, 2-propanol, 1-butanol, 2-butanol, tert-butyl alcohol, 1-, 2-, or 3-pentanol, neo-pentyl alcohol, and the like; esters such as ethyl acetate, isopropyl acetate, and the like; ketones such as acetone and the like; aromatic hydrocarbons such as benzene, toluene, and xylene, or alkanes such as cyclohexane, pentane, hexane, heptane, and the like. Additional organic solvents that can be used in the reactions described herein include polar organic solvents including, but not limited to, acetonitrile, dimethylformamide, dimethylacetamide, dimethyl sulfoxide, ethyl acetate, alcohols, and the like. When polar organic solvents (e.g., alcohols, acetonitrile, DMF, N-methylpyrrolidinone, nitromethane) contain water they are referred to herein as aqueous organic solvent. Depending on the nature of the reaction step, solvents that are suitable for the particular reaction step can be readily selected by a person skilled in the art.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry, or mass spectrometry; or by chromatography such as high-performance liquid chromatography (HPLC) or thin layer chromatography. The compounds obtained by the reactions can be purified by any suitable method known in the art. For example, chromatography (medium pressure) on a suitable adsorbent (e.g., silica gel, alumina, and the like), HPLC, or preparative thin layer chromatography; distillation; sublimation, trituration, or recrystallization. The purity of the compounds, in general, are determined by physical methods such as measuring the melting point (in case of a solid), obtaining an NMR spectrum, or performing a HPLC separation.

"Alcohol" refers to an aliphatic hydrocarbon compound that carries one or more such as 1 or 2 hydroxy group. Representative examples include, but are not limited to, methanol, ethanol, propanol, butanol, 1,2-propanediol, and the like.

A "pharmaceutically acceptable salt" of a compound means a salt that is pharmaceutically acceptable and that possesses the desired pharmacological activity of the parent compound. Such salts include:

acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in *Remington's Pharmaceutical Sciences,* 17th ed., Mack Publishing Company, Easton, PA, 1985, which is incorporated herein by reference in its entirety.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

The term "optionally" or "optional" as used herein means that the subsequently described event or circumstance may but need not occur, and that the description includes instances where the event or circumstance occurs and instances in which it does not. For example, the phrase "optionally converting the amine solvate of Compound 1 from any one of Steps (a1) to (c1) to Compound 1" in Step (d1) of the fourth aspect of the Summary means that the process described in the fourth aspect may or may not include a step where the amine solvate of Compound 1 from any one of Steps (a1) to (c1) is converted to Compound 1.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass ±10%, preferably ±5%, the recited value and the range is included.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a disease or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

"Treating" or "treatment" of a disease includes:
(1) inhibiting the disease, i.e., arresting (i.e., stabilizing) or reducing the development of the disease or its clinical symptoms; or
(3) relieving the disease, i.e., causing regression of the disease or its clinical symptoms.

A "therapeutically effective amount" means the amount of a compound of the present disclosure or a pharmaceutically acceptable salt thereof that, when administered to a patient for treating a disease, is sufficient to affect such treatment for the disease. The "therapeutically effective amount" will vary depending on the compound, the disease and its severity and the age, weight, etc., of the mammal to be treated.

EMBODIMENTS

In the embodiments below, a numerical range of embodiments, may refer to a numbering range of another embodiments. By way of example, in Embodiment D below, process embodiments D47-D54 refer to numerical range of embodiments C2 to C9 respectively, of composition of matter Embodiment C, and embodiments D60-69 refer to numerical range of embodiments A2 to A11, respectively, of composition of matter Embodiment A. This means that process embodiments D47-D54 produce, respectively, the product embodiments C2-C9, namely process embodiment D47 produces the product according to embodiment C2, process embodiment C48 produces the product according to embodiment C3, etc. Similarly, process embodiment D60 produces the product according to embodiment A2, process embodiment D69 produces the product according to embodiment A11.

In further embodiments, the present disclosure includes:

Embodiment A

A1. In embodiment A1, provided is a crystalline Form A polymorph of Compound 1 having an X-ray powder diffraction pattern as described in the first aspect in the Summary.

A2. In embodiment A2, the crystalline Form A polymorph of embodiment A1, is wherein the Form A X-ray powder diffraction pattern further comprises a peak at angular position 20.1, wherein the angular positions may vary by ±0.2° 2θ.

A3. In embodiment A3, the crystalline Form A polymorph of embodiment A1, is wherein the Form A X-ray powder diffraction pattern further comprises peaks at angular positions 12.9 and 20.1, wherein the angular positions may vary by ±0.2° 2θ.

A4. In embodiment A4, the crystalline Form A polymorph of embodiment A1, is wherein the Form A X-ray powder diffraction pattern further comprises peaks at angular positions 11.4, 12.9, and 20.1, wherein the angular positions may vary by ±0.2° 2θ.

A5. In embodiment A5, the crystalline Form A polymorph of embodiment A1, is wherein the Form A X-ray powder diffraction pattern further comprises peaks at angular positions 10.1, 11.4, 12.9, and 20.1, wherein the angular positions may vary by ±0.2° 2θ.

A6. In embodiment A6, provided is a crystalline Form A polymorph of Compound 1 having an X-ray powder diffraction pattern comprising at least two, at least three, at least four, at least five, at least six peaks, at least seven peaks, or at least eight peaks at angular positions selected from Table 1 below, wherein the angular positions may vary by ±0.2° 2θ.

TABLE 1

| Angle (2-Theta °) | d value (Å) | Intensity % |
|---|---|---|
| 9.2 | 9.59 | 6.9 |
| 10.1 | 8.79 | 19.5 |
| 11.4 | 7.75 | 21.6 |
| 12.9 | 6.87 | 21.6 |
| 13.7 | 6.48 | 15.2 |
| 14.0 | 6.33 | 3.5 |

TABLE 1-continued

| Angle (2-Theta °) | d value (Å) | Intensity % |
|---|---|---|
| 15.4 | 5.75 | 3.8 |
| 15.8 | 5.59 | 100 |
| 16.6 | 5.35 | 9.8 |
| 17.4 | 5.09 | 6.7 |
| 18.0 | 4.93 | 10.2 |
| 18.6 | 4.77 | 25.3 |
| 19.6 | 4.53 | 15.3 |
| 20.1 | 4.41 | 24.3 |
| 20.7 | 4.29 | 4 |
| 21.0 | 4.23 | 3.9 |
| 21.4 | 4.15 | 13.2 |
| 21.7 | 4.09 | 18.5 |
| 22.1 | 4.03 | 10.6 |
| 22.6 | 3.94 | 5.3 |
| 23.8 | 3.74 | 3 |
| 24.1 | 3.69 | 4.5 |
| 25.0 | 3.55 | 14.7 |
| 26.0 | 3.43 | 13.9 |
| 26.7 | 3.33 | 3.4 |
| 27.2 | 3.28 | 6.4 |
| 27.6 | 3.23 | 4.4 |
| 27.8 | 3.20 | 3.8 |
| 28.2 | 3.16 | 7.3 |
| 29.0 | 3.07 | 6.2 |
| 29.6 | 3.02 | 9.3 |
| 30.1 | 2.97 | 4.4 |
| 30.6 | 2.92 | 3 |
| 31.0 | 2.88 | 2.9 |
| 31.7 | 2.82 | 3.5 |
| 31.9 | 2.80 | 4 |
| 32.4 | 2.76 | 5.1 |
| 33.6 | 2.66 | 5.4 |
| 34.2 | 2.62 | 3.3 |
| 34.6 | 2.59 | 4.3 |
| 35.4 | 2.53 | 3.2 |
| 35.8 | 2.50 | 3.3 |

A7. In embodiment A7, the crystalline Form A polymorph of embodiment A6, is wherein the at least two, at least three, at least four, at least five, or at least six peaks are selected from 10.1, 11.4, 12.9, 13.7, 15.8, 18.6, 19.6, 20.1, 21.4, 21.7, 25.0, and 26.0, wherein the angular positions may vary by ±0.2° 2θ. In an embodiment of A6, the at least two, at least three, at least four, at least five, or at least six peaks are selected from 10.1, 11.4, 12.9, 13.7, 15.8, 18.0, 19.6, 20.1, 21.4, 21.7, 25.0, and 26.0, wherein the angular positions may vary by ±0.2° 2θ.

Figure 3:
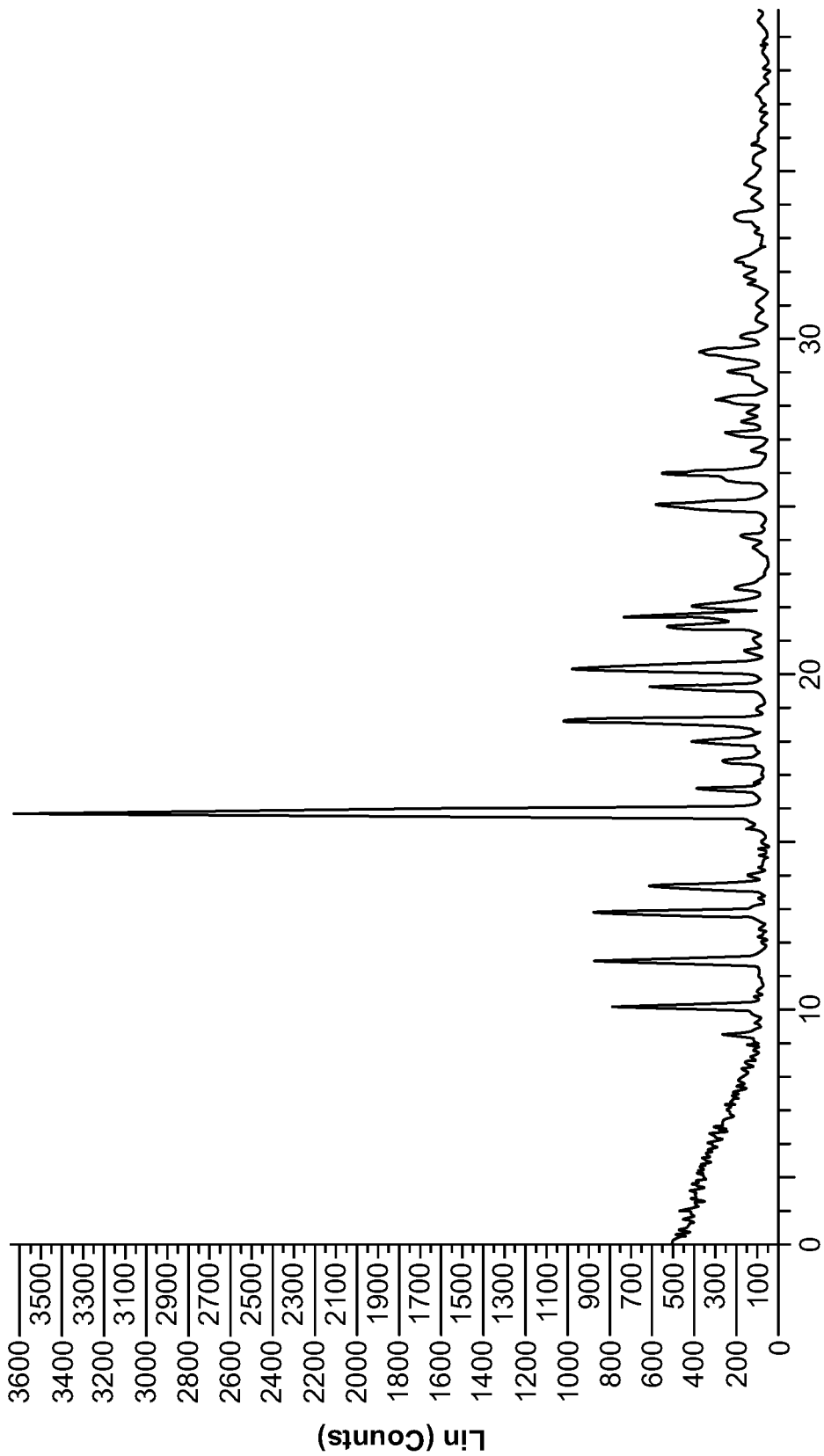
FIG. 3 depicts a representative XRPD diffractogram of crystalline Form A polymorph of Compound 1, prepared according to the method described in Example 3.
Figure 4:
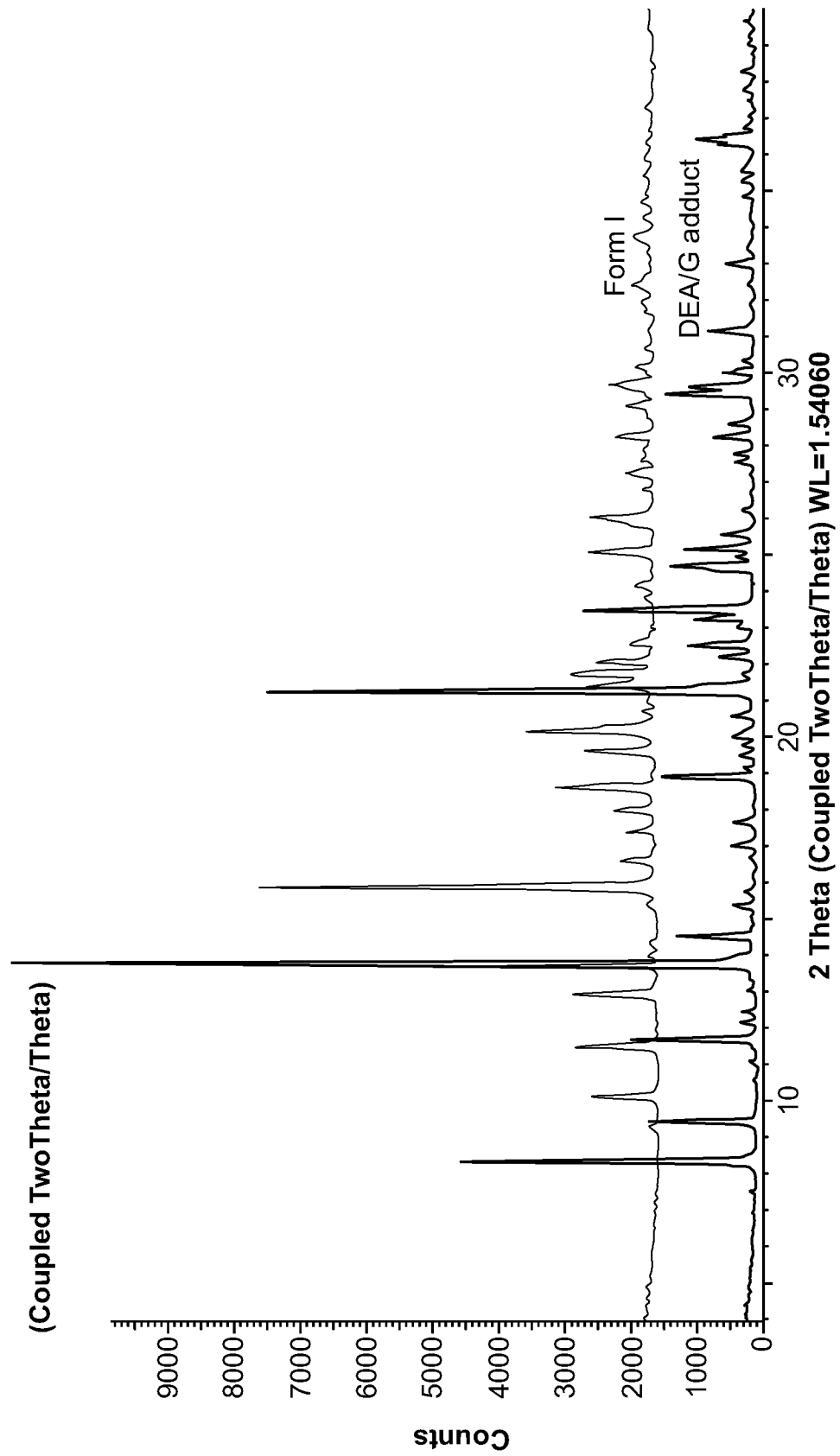
FIG. 4 depicts a comparative XRPD diffractograms of crystalline Form A polymorph of Compound 1, prepared according to the method described in Example 3, and Form B polymorph of a diethylamine solvate of Compound 1, prepared according to method described in Example 4.

A8. In embodiment A8, provided is a crystalline Form A polymorph of Compound 1 having an X-ray powder diffraction pattern substantially identical as shown in FIG. 3.

A9. In embodiment A9, the crystalline Form A polymorph of any one of A1 to A8, are wherein the angular positions of the X-ray diffraction peaks denoted therein may vary by ±0.1° 2θ.

A10. In embodiment A10, the crystalline Form A polymorph of any one of A1 to A9, is substantially pure.

A11. In embodiment A10, the crystalline Form A polymorph of any one of A1 to A10, is substantially free of 3-fluoro-5-(((1R,2aS)-1,3,3,4,4-pentafluoro-2a-hydroxy-2,2a,3,4-tetrahydro-1H-cyclopenta[cd]inden-7-yl)oxy)benzonitrile enantiomer of Compound 1.

Embodiment B

B1. In embodiment B1, provided is an amine solvate of Compound 1 as defined in the second aspect of the Summary.

B2. In embodiment B2, the amine solvate of embodiment B1, is wherein the amine is $NHR^1R^2$.

B3. In embodiment B3, the amine solvate of embodiment B1, is wherein the amine is $R^3R^4$—N—$(CH_2)_n$—$NR^5R^6$.

B4. In embodiment B4, the amine solvate of embodiment B1 or B2, is wherein $R^1$ is hydrogen and $R^2$ is $C_2$-$C_{12}$ alkyl, $C_2$-$C_6$ alkenyl, $C_2$-$C_6$ alkynyl, $C_3$-$C_7$ cycloalkyl, or $C_3$-$C_7$ cycloalkyl-$C_{1-6}$ alkyl.

B5. In embodiment B5, the amine solvate of embodiment B1, B2, or B4, is wherein $R^1$ is hydrogen and $R^2$ is $C_2$-$C_{12}$ alkyl.

B6. In embodiment B6, the amine solvate of embodiment B1, B2, or B4, is wherein $R^1$ is hydrogen and $R^2$ is $C_3$-$C_7$ cycloalkyl.

B6A. In embodiment B6A, the amine solvate of embodiment B1, B2, or B4, is wherein $R^1$ is hydrogen and $R^2$ is $C_3$-$C_7$ cycloalkyl-$C_{1-6}$ alkyl.

B7. In embodiment B7, the amine solvate of embodiment B1 or B2, is wherein $R^1$ is $C_1$-$C_6$ alkyl, $C_2$-$C_6$ alkenyl, or $C_2$-$C_6$ alkynyl and $R^2$ is $C_1$-$C_6$ alkyl, $C_2$-$C_6$ alkenyl, $C_2$-$C_6$ alkynyl, $C_3$-$C_7$ cycloalkyl, or $C_3$-$C_7$ cycloalkyl-$C_{1-6}$ alkyl.

B8. In embodiment B8, the amine solvate of embodiment B1, B2, or B7, is wherein $R^1$ is $C_1$-$C_6$ alkyl and $R^2$ is $C_1$-$C_6$ alkyl.

B9. In embodiment B9, the amine solvate of embodiment B1, B2, or B7, is wherein $R^1$ is $C_1$-$C_6$ alkyl and $R^2$ is $C_3$-$C_7$ cycloalkyl.

B10. In embodiment B10, the amine solvate of embodiment Bi, B2, or B7, is wherein $R^1$ is $C_1$-$C_6$ alkyl and $R^2$ is $C_3$-$C_7$ cycloalkyl-$C_{1-6}$ alkyl.

B10A. In embodiment B10A, the amine solvate of embodiment B1 or B2, is wherein $R^1$ and $R^2$ are independently $C_3$-$C_7$ cycloalkyl-$C_{1-6}$ alkyl.

B11. In embodiment B11, the amine solvate of embodiment Bi or B2, is wherein $R^1$ and $R^2$ together with the nitrogen atom to which they are attached form cyclylamine.

B12. In embodiment B12, the amine solvate of embodiment Bi or B3, is wherein n is selected from 2 to 5. In a first embodiment of B12, n is 3 to 5. In a second embodiment of B12, n is 4 or 5.

B13. In embodiment B13, the amine solvate of embodiment B1 or B3, is wherein n is selected from 2 to 4. In a first embodiment of B13, n is 3 or 4. In a second embodiment of B13, n is 3.

B14. In embodiment B14, the amine solvate of embodiment B1 or B3, is wherein n is 2 or 3.

B15. In embodiment B15, the amine solvate of embodiment B1 or B3, is wherein n is 2.

B16. In embodiment B16, the amine solvate of any one of embodiments B1, B3, and B12 to B15 and subembodiments contained therein, is wherein $R^3$ is hydrogen.

B17. In embodiment B17, the amine solvate of any one of embodiments Bi, B3, and B12 to B15 and subembodiments contained therein, is wherein $R^3$ is $C_1$-$C_6$ alkyl.

B18. In embodiment B18, the amine solvate of any one of embodiments B1, B3, and B12 to B15 and subembodiments contained therein, is wherein $R^3$ is $C_3$-$C_7$ cycloalkyl.

B19. In embodiment B19, the amine solvate of any one of embodiments B1, B3, and B12 to B18 and subembodiments contained therein, is wherein $R^4$ is hydrogen.

B20. In embodiment B20, the amine solvate of any one of embodiments B1, B3, and B12 to B18 and subembodiments contained therein, is wherein $R^4$ is $C_1$-$C_6$ alkyl.

B21. In embodiment B21, the amine solvate of any one of embodiments B1, B3, and B12 to B18 and subembodiments contained therein, is wherein $R^4$ is $C_3$-$C_7$ cycloalkyl.

B22. In embodiment B22, the amine solvate of any one of embodiments B1, B3, and B12 to B21 and subembodiments contained therein, is wherein $R^5$ is hydrogen.

B23. In embodiment B23, the amine solvate of any one of embodiments B1, B3, and B12 to B21 and subembodiments contained therein, is wherein $R^5$ is $C_1$-$C_6$ alkyl.

B24. In embodiment B24, the amine solvate of any one of embodiments B1, B3, and B12 to B21 and subembodiments contained therein, is wherein $R^5$ is $C_3$-$C_7$ cycloalkyl.

B25. In embodiment B25, the amine solvate of any one of embodiments B1, B3, and B12 to B24 and subembodiments contained therein, is wherein $R^6$ is hydrogen.

B26. In embodiment B26, the amine solvate of any one of embodiments B1, B3, and B12 to B24 and subembodiments contained therein, is wherein $R^6$ is $C_1$-$C_6$ alkyl.

B27. In embodiment B27, the amine solvate of any one of embodiments B1, B3, and B12 to B24 and subembodiments contained therein, is wherein $R^6$ is $C_3$-$C_7$ cycloalkyl.

B28. In embodiment B28, the amine solvate of any one of embodiments B1, B2, and B4, to B6A is wherein the amine is ethylamine, n-propylamine, isopropylamine, n-butylamine, sec-butylamine, tert-butylamine, n-pentylamine, sec-pentylamine, pentyl-3-amine, neopentyl-amine, n-hexylamine, 2-hexylamine, 3-hexylamine, isohexylamine, 1-methylpentylamine, 2-ethylbutylamine, 2-methylpentylamine, 1,1-dimethylbutylamine, 1,3-dimethylbutylamine, 3,3-dimethylbutylamine, 2-methyl-3-pentylamine, 3-methylpentylamine, 3-methyl-3-pentylamine, 3-methyl-2-pentylamine, 2-methylbutylamine, 1,2,2-trimethylpropylamine, cyclopropylamine, cyclobutylamine, cyclopentylamine, cyclohexylamine, cyclobutylmethylamine, cyclopropylmethylamine, 2-methylcyclopropylamine, 2-cyclopropylethylamine, 2-methylcyclopentylamine, 3-methylcyclopentylamine, cyclopentylmethylamine, 2-cyclobutylethylamine, 3-cyclopropyl-propylamine, 2-ethylcyclopropylamine, allyamine or propargylamine.

B29. In embodiment B29, the amine solvate of any one of embodiments B1, B2, B4, and B5 is wherein the amine is ethylamine, n-propylamine, isopropylamine, n-butylamine, sec-butylamine, tert-butylamine, n-pentylamine, sec-pentylamine, pentyl-3-amine, neopentyl-amine, n-hexylamine, 2-hexylamine, 3-hexylamine, isohexylamine, 1-methylpentylamine, 2-ethylbutylamine, 2-butylamine, 2-methylpentylamine, 1,1-dimethylbutylamine, 1,3-dimethylbutylamine, 3,3-dimethylbutylamine, 2-methyl-3-pentylamine, 3-methylpentylamine, 3-methyl-3-pentylamine, 3-methyl-2-pentylamine, 2-methylbutyl-1-amine, or 1,2,2-trimethyl-propylamine.

B30. In embodiment B30, the amine solvate of any one of embodiments B1, B2, B4, and B6 is wherein the amine is cyclopropylamine, cyclobutylamine, cyclopentylamine, cyclohexyl-amine, 2-methylcyclopropylamine, 2-methylcyclopentylamine, 3-methyl-cyclopentylamine, or 2-ethylcyclopropylamine.

B31. In embodiment B31, the amine solvate of any one of embodiments B1, B2, and B7 to B10 is wherein the amine is N-methylethylamine, diethylamine, N-methyl-n-propylamine, N-methylisopropylamine, N-allylmethylamine, N-methylpropargylamine, N-ethyl-n-propylamine, N-ethyl-isopropylamine, N-methylbutylamine, N-methyl-2-butylamine, N-tert-butyl-methyl-amine, N-methyl-cyclobutylamine, N-ethylcyclopropylamine, 1-cyclopropyl-N-methylmethanamine, N-ethyl-prop-2-yn-1-amine, N-ethylallylamine, N-methylpentylamine, N-methyl-2-pentylamine, N-methyl-3-pentylamine, N,3-dimethylbutane-2-amine, N,2-dimethyl-butane-2-amine, N,3-dimethylbutane-2-amine, N-methylcyclopentylamine, N-ethyl-1-butylamine, N-ethyl-2-butylamine, N-ethyl-2-methyl-2-propylamine, N-ethyl-2-methylpropylamine, N-ethylcyclobutylamine, di-n-propylamine, di-isopropylamine, N-isopropylpropylamine, diallylamine, dipropargylamine, or allylpropargylamine. In one embodiment of B31, the amine is not diethylamine.

B32. In embodiment B32, the amine solvate of any one of embodiments B1, B2, B7, and B8 is wherein the amine is N-methylethylamine, diethylamine, N-methyl-n-propylamine, N-methyl-isopropylamine, N-ethyl-n-propylamine, N-ethyl-isopropylamine, N-methylbutylamine, N-methyl-2-butylamine, N-tert-butyl-methyl-amine, N-methylpentyl-1-amine, N-methyl-2-pentylamine, N-methyl-3-pentylamine, N,3-dimethylbutane-2-amine, N,2-dimethylbutane-2-amine, N,3-dimethylbutane-2-amine, N-ethyl-1-butylamine, N-ethyl-2-butylamine, N-ethyl-2-methyl-2-propylamine, N-ethyl-2-methylpropylamine, di-n-propylamine, di-isopropylamine, or N-isopropylpropylamine. In one embodiment of B32, the amine is not diethylamine.

B33. In embodiment B33, the amine solvate of any one of embodiments B1, B2, B7, and B9 is wherein the amine is N-methylcyclobutylamine, N-ethylcyclopropylamine, N-methylcyclopentylamine, or N-ethylcyclobutylamine.

B34. In embodiment B34, the amine solvate of any one of embodiments B1, B2, and B11 is wherein the amine is azetidine, pyrrolidine, piperidine, piperazine, morpholine, azepane, or azocane.

B35. In embodiment B35, the amine solvate of any one of embodiments B1, B3, and B12 to B16, B19, B20, B22, B23, and B25, is wherein the amine is ethylenendiamine, propane-1,3-diamine, butane-1,4-diamine, pentane-1,5-diamine, hexane-1,6-diamine, $N^1,N^2$-dimethylethane-1,2-diamine, or $N^1,N^2$-diethylethane-1,2-diamine.

B36. In embodiment B36, the amine solvate of embodiment B1 or B2 is wherein the amine is N-methylethylamine, diethylamine, N-methyl-n-propylamine, N-methyl-isopropylamine, N-ethyl-n-propylamine, N-ethyl-isopropylamine, azetidine, pyrrolidine, piperidine, or morpholine.

B37. In embodiment B37, the amine solvate of embodiment Bi or B36, is wherein the amine is diethylamine.

B38. In embodiment B38, the amine solvate of embodiment B37, is wherein the stoichiometric ratio of diethylamine to Compound 1 in the diethylamine solvate of Compound 1 is about 1:1.

B39. In embodiment B39, the amine solvate of any one of embodiments B1 to B38, is wherein the amine solvate of Compound 1 is a solid.

B39A. In embodiment B39A, the amine solvate of embodiment B37, B38, or B39, is wherein the amine solvate of Compound 1 is a crystalline solid.

B40. In embodiment B40, the amine solvate of any one of embodiments B1 to B38, is wherein the amine solvate of Compound 1 is present in situ.

B41. In embodiment B41, the amine solvate of embodiment B40, is wherein the amine solvate of Compound 1 is present in a mixture comprising, one or more suitable organic solvents, Compound 1, and the amine.

B42. In embodiment B42, the amine solvate of embodiment B37, is wherein the diethylamine solvate of Compound 1 is present in a mixture comprising, one or more suitable organic solvent, Compound 1, and diethylamine.

B43. In embodiment B43, the amine solvate of any one of embodiments B40 to B42, is wherein the one or more suitable organic solvents are a polar organic solvent independently selected from ethers, alcohols, esters, halogenated alkanes, ketones, dimethylformamide, dimethylacetamide, acetonitrile, nitromethane, n-methyl pyrrolidinone, toluene, and xylene.

B43a. In embodiment B43a, the amine solvate of any one of embodiments B40 to B43, is wherein the one or more suitable organic solvents are a polar organic solvent independently selected from ethers, esters, halogenated alkanes, ketones, dimethylformamide, dimethylacetamide, acetonitrile, nitromethane, n-methyl pyrrolidinone, toluene, and xylene.

B44. In embodiment B44, the amine solvate of embodiment B43, is wherein the one or more suitable organic solvents are independently selected from n-pentanol, methanol (MeOH), ethanol, n-propanol, isopropanol (IPA), n-butanol, 1,2-propanediol, methylene dichloride, chloroform, 1,2-dichloroethane, diethyl ether, diisopropyl ether, methyl tert-butyl ether (MTBE), methyl tert-amyl ether, methyl acetate (MeOAc), ethyl acetate (EtOAc), n-propylacetate, isopropylacetate (IPAc), butyl acetate, n-methyl pyrrolidinone (NMP), dimethyl formamide (DMF), dimethylacetamide (DMAC), tetrahydrofuran (THF), 2-methyl THF (2-MeTHF), dimethoxyethane (DME), toluene, acetone, methyl ethyl ketone (MEK), nitromethane, acetonitrile (ACN), and 1,4-dioxane.

B44a. In embodiment B44a, the amine solvate of embodiment B44, is wherein the one or more suitable organic solvents are independently selected from n-pentanol, methanol (MeOH), n-propanol, isopropanol (IPA), n-butanol, 1,2-propanediol, methylene dichloride, chloroform, 1,2-dichloroethane, diethyl ether, diisopropyl ether, methyl tert-butyl ether (MTBE), methyl tert-amyl ether, methyl acetate (MeOAc), ethyl acetate (EtOAc), n-propylacetate, isopropylacetate (IPAc), butyl acetate, n-methyl pyrrolidinone (NMP), dimethyl formamide (DMF), dimethylacetamide (DMAC), tetrahydrofuran (THF), 2-methyl THF (2-MeTHF), dimethoxyethane (DME), toluene, acetone, methyl ethyl ketone (MEK), nitromethane, acetonitrile (ACN), and 1,4-dioxane.

B44b. In embodiment B44b, the amine solvate of embodiment B43a, is wherein the one or more suitable organic solvents are independently selected from methylene dichloride, chloroform, 1,2-dichloroethane, diethyl ether, diisopropyl ether, methyl tert-butyl ether (MTBE), methyl tert-amyl ether, methyl acetate (MeOAc), ethyl acetate (EtOAc), n-propylacetate, isopropylacetate (IPAc), butyl acetate, n-methyl pyrrolidinone (NMP), dimethyl formamide (DMF), dimethylacetamide (DMAC), tetrahydrofuran (THF), 2-methyl THF (2-MeTHF), dimethoxyethane (DME), toluene, acetone, methyl ethyl ketone (MEK), nitromethane, acetonitrile (ACN), and 1,4-dioxane.

B45. In embodiment B45, the amine solvate of embodiment B43 to B44b, is wherein the suitable organic solvent is methyl tert-butyl ether.

Embodiment C

C1. In embodiment C1, provided is a crystalline Form B polymorph of a diethylamine solvate of Compound 1 having an X-ray powder diffraction pattern as described in the third aspect in the Summary.

C2. In embodiment C2, the crystalline Form B of embodiment C1, is wherein the Form B X-ray powder diffraction pattern further comprises a peak at angular position 8.4, wherein the angular positions may vary by ±0.2° 2θ.

C3. In embodiment C3, the crystalline Form B of embodiment C1, is wherein the Form B X-ray powder diffraction pattern further comprises peaks at angular positions 8.4 and 23.5, wherein the angular positions may vary by ±0.2° 2θ.

C4. In embodiment C4, the crystalline Form B of embodiment C1, is wherein the Form B X-ray powder diffraction pattern further comprises peaks at angular positions 8.4, 23.5, and 11.7, wherein the angular positions may vary by ±0.2° 2θ.

C5. In embodiment C5, the crystalline Form B of embodiment C1, is wherein the Form B X-ray powder diffraction pattern further comprises peaks at angular positions 8.4, 23.5, 11.7, and 9.5, wherein the angular positions may vary by ±0.2° 2θ.

C6. In embodiment C6, provided is a crystalline Form B polymorph of the diethylamine solvate of Compound 1 having an X-ray powder diffraction pattern comprising at least two, at least three, at least four, at least five, at least six, at least seven, or at least eight peaks at angular positions selected from in Table 2 below, wherein the angular positions may vary by ±0.2° 2θ.

TABLE 2

| Angle (2-Theta °) | d value (Å) | Intensity % |
|---|---|---|
| 7.5 | 11.71 | 0.6 |
| 8.4 | 10.57 | 28.0 |
| 9.5 | 9.35 | 10.3 |
| 10.6 | 8.35 | 0.2 |
| 11.1 | 7.98 | 0.5 |
| 11.7 | 7.55 | 12.1 |
| 12.2 | 7.27 | 1.3 |
| 12.5 | 7.10 | 1.3 |
| 13.1 | 6.77 | 0.5 |
| 13.4 | 6.61 | 0.6 |
| 13.8 | 6.41 | 100.0 |
| 14.6 | 6.06 | 7.5 |
| 15.4 | 5.74 | 1.8 |
| 15.8 | 5.61 | 0.6 |
| 16.7 | 5.29 | 0.5 |
| 17.1 | 5.19 | 2.1 |
| 17.7 | 5.00 | 1.9 |
| 19.0 | 4.68 | 8.9 |
| 19.2 | 4.61 | 0.7 |
| 19.5 | 4.54 | 1.2 |
| 19.8 | 4.47 | 0.6 |
| 20.1 | 4.41 | 1.6 |
| 20.6 | 4.30 | 2.0 |
| 21.3 | 4.17 | 46.2 |
| 21.8 | 4.08 | 0.8 |
| 22.3 | 3.99 | 2.8 |
| 22.6 | 3.94 | 6.0 |
| 23.1 | 3.85 | 1.1 |
| 23.3 | 3.82 | 5.5 |
| 23.5 | 3.78 | 16.0 |
| 24.7 | 3.60 | 7.9 |
| 25.2 | 3.53 | 6.3 |
| 25.6 | 3.48 | 3.0 |
| 26.3 | 3.39 | 0.9 |
| 26.7 | 3.33 | 0.3 |
| 27.2 | 3.27 | 0.4 |
| 27.6 | 3.23 | 1.2 |
| 27.8 | 3.21 | 1.6 |
| 28.2 | 3.16 | 3.8 |
| 28.6 | 3.12 | 2.3 |
| 29.5 | 3.03 | 5.8 |
| 29.6 | 3.02 | 3.8 |
| 30.0 | 2.98 | 3.0 |
| 30.4 | 2.94 | 0.6 |
| 31.1 | 2.87 | 4.4 |
| 31.9 | 2.81 | 0.5 |
| 32.4 | 2.76 | 0.5 |
| 33.0 | 2.72 | 2.7 |
| 33.5 | 2.68 | 0.4 |
| 34.3 | 2.61 | 0.4 |
| 34.9 | 2.57 | 0.9 |
| 35.3 | 2.54 | 0.9 |
| 35.6 | 2.52 | 0.8 |
| 36.4 | 2.46 | 5.5 |
| 36.8 | 2.44 | 0.8 |
| 37.8 | 2.38 | 1.0 |
| 38.3 | 2.35 | 1.3 |

TABLE 2-continued

| Angle (2-Theta °) | d value (Å) | Intensity % |
|---|---|---|
| 39.2 | 2.30 | 0.3 |
| 39.3 | 2.29 | 0.5 |
| 39.6 | 2.27 | 0.6 |

C7. In embodiment C7, the crystalline Form B of embodiment C6, is wherein the at least two, at least three, at least four, at least five, or six peaks are selected from 8.4, 9.5, 11.7, 13.8, 21.3, and 23.5 wherein the angular positions may vary by ±0.2° 2θ.

C8. In embodiment C8, provided is a crystalline Form B of polymorph of the diethylamine solvate of Compound 1 having an X-ray powder diffraction pattern substantially identical as shown in FIG. 1.

C9. In embodiment C9, the crystalline Form B of any one of C1 to C8, are wherein the peaks denoted therein have margin of error of ±0.1° 2θ.

Embodiment D

D1. In embodiment D1, provided is a process of preparing an amine solvate of Compound 1 as described in the fourth aspect of the Summary.

D2. In embodiment D2, the process of embodiment D1, is wherein Compound 1 is contacted with the amine by adding Compound 1 to the amine or by adding the amine to a mixture of Compound 1 in one or more suitable organic solvents in Step (a1).

D3. In embodiment D3, the process of embodiment D1 or D2, is wherein the Compound 1 is contacted with the amine by adding the amine to a mixture of Compound 1 in one or more suitable organic solvents in Step (a1).

D4. In embodiment D4, the process of any one of embodiments D1 to D3, is wherein the amine is $NHR^1R^2$.

D5. In embodiment D5, the process of any one of embodiments D1 to D3, is wherein the amine is $R^3R^4-N-(CH_2)_n-NR^5R^6$.

D5A. In embodiment D5A, the process of any one of embodiments D1 to D4, is wherein $R^1$ is hydrogen and $R^2$ is $C_2-C_{12}$ alkyl, $C_2-C_6$ alkenyl, $C_2-C_6$ alkynyl, $C_3-C_7$ cycloalkyl, or $C_3-C_7$ cycloalkyl-$C_{1-6}$ alkyl.

D6. In embodiment D6, the process of any one of embodiments D1 to D4 and D5A, is wherein $R^1$ is hydrogen and $R^2$ is $C_2-C_{12}$ alkyl.

D7. In embodiment D7, the process of any one of embodiments D1 to D4 and D5A, is wherein $R^1$ is hydrogen and $R^2$ is $C_3-C_7$ cycloalkyl.

D7A. In embodiment D7A, the process of any one of embodiments D1 to D4 and D5A, is wherein $R^1$ is hydrogen and $R^2$ is $C_3-C_7$ cycloalkyl-$C_{1-6}$ alkyl.

D7B. In embodiment D7B, the process of any one of embodiments D1 to D4, is wherein $R^1$ is $C_1-C_6$ alkyl, $C_2-C_6$ alkenyl, or $C_2-C_6$ alkynyl and $R^2$ is $C_1-C_6$ alkyl, $C_2-C_6$ alkenyl, $C_2-C_6$ alkynyl, $C_3-C_7$ cycloalkyl, or $C_3-C_7$ cycloalkyl-$C_{1-6}$ alkyl.

D8. In embodiment D8, the process of any one of embodiments D1 to D4, and D7B, is wherein $R^1$ is $C_1-C_6$ alkyl and $R^2$ is $C_1-C_6$ alkyl.

D9. In embodiment D9, the process of any one of embodiments D1 to D4, and D7B, is wherein $R^1$ is $C_1-C_6$ alkyl and $R^2$ is $C_3-C_7$ cycloalkyl.

D10. In embodiment D10, process of any one of embodiments D1 to D4, and D7B, is wherein $R^1$ is $C_1-C_6$ alkyl and $R^2$ is $C_3-C_7$ cycloalkyl-$C_{1-6}$ alkyl.

D10A. In embodiment D10A, the process of any one of embodiments D1 to D4, is wherein $R^1$ and $R^2$ are independently $C_3-C_7$ cycloalkyl-$C_{1-6}$ alkyl.

D11. In embodiment D11, the process of any one of embodiments D1 to D4, is wherein $R^1$ and $R^2$ together with the nitrogen atom to which they are attached form cyclylamine.

D12. In embodiment D12, the process of any one of embodiments D1 to D3 and D5, is wherein n is selected from 2 to 5. In a first embodiment of D12, n is 3 to 5. In a second embodiment of D12, n is 4 or 5.

D13. In embodiment D13, the process of any one of embodiments D1 to D3 and D5, is wherein n is selected from 2 to 4. In a first embodiment of D13, n is 3 or 4. In a second embodiment of D13, n is 3.

D14. In embodiment D14, the process of any one of embodiments D1 to D3 and D5, is wherein n is 2 or 3.

D15. In embodiment D15, the process of any one of embodiments D1 to D3 and D5, is wherein n is 2.

D16. In embodiment D16, the process of any one of embodiments D1 to D3 and D12 to D15 and subembodiments contained therein, is wherein $R^3$ is hydrogen.

D17. In embodiment D17, the process of any one of embodiments D1 to D3 and D12 to D15 and subembodiments contained therein, is wherein $R^3$ is $C_1-C_6$ alkyl.

D18. In embodiment D18, the process of any one of embodiments D1 to D3 and D12 to D15 and subembodiments contained therein, is wherein $R^3$ is $C_3-C_7$ cycloalkyl.

D19. In embodiment D19, the process of any one of embodiments D1 to D3 and D12 to D18 and subembodiments contained therein, is wherein $R^4$ is hydrogen.

D20. In embodiment D20, the process of any one of embodiments D1 to D3 and D12 to D18 and subembodiments contained therein, is wherein $R^4$ is $C_1-C_6$ alkyl.

D21. In embodiment D21, the process of any one of embodiments D1 to D3 and D12 to D18 and subembodiments contained therein, is wherein $R^4$ is $C_3-C_7$ cycloalkyl.

D22. In embodiment D22, the process of any one of embodiments D1 to D3 and D12 to D21 and subembodiments contained therein, is wherein $R^5$ is hydrogen.

D23. In embodiment D23, the process of any one of embodiments D1 to D3 and D12 to D21 and subembodiments contained therein, is wherein $R^5$ is $C_1-C_6$ alkyl.

D24. In embodiment D24, the process of any one of embodiments D1 and D3 and D12 to D21 and subembodiments contained therein, is wherein $R^5$ is $C_3-C_7$ cycloalkyl.

D25. In embodiment D25, the process of any one of embodiments D1 to D3 and D12 to D24 and subembodiments contained therein, is wherein $R^6$ is hydrogen.

D26. In embodiment D26, the process of any one of embodiments D1 to D3 and D12 to D24 and subembodiments contained therein, is wherein $R^6$ is $C_1-C_6$ alkyl.

D27. In embodiment D27, the process of any one of embodiments D1 to D3 and D12 to D24 and subembodiments contained therein, is wherein $R^6$ is $C_3-C_7$ cycloalkyl.

D28. In embodiment D28, the process of any one of embodiments D1 to D4 and D5A to D7 is wherein the amine is ethylamine, n-propylamine, isopropylamine, n-butylamine, sec-butylamine, tert-butylamine, n-pentylamine, sec-pentylamine, pentyl-3-amine, neopentylamine, n-hexylamine, 2-hexylamine, 3-hexylamine, isohexylamine, 1-methylpentylamine, 2-ethylbutylamine, 2-methylpentylamine, 1,1-dimethylbutylamine, 1,3-dimethylbutylamine, 3,3-dimethylbutylamine, 2-methyl-3-pentylamine, 3-methylpentylamine, 3-methyl-3-pentylamine, 3-methyl-2-pentylamine, 2-methylbutylamine, 1,2,2-trimethylpropylamine, cyclopropylamine, cyclobutylamine, cyclopentylamine, cyclohexylamine, cyclobutylmethylamine, cyclopropylmethylamine, 2-methylcyclopropylamine, 2-cyclopropylethylamine, 2-methyl-cyclopentylamine, 3-methylcyclopentylamine, cyclopentylmethylamine, 2-cyclobutylethylamine, 3-cyclopropylpropyl-amine, 2-ethylcyclopropylamine, allyamine or propargylamine.

D29. In embodiment D29, the process of any one of embodiments D1 to D4, D5A and D6 is wherein the amine is ethylamine, n-propylamine, isopropylamine, n-butylamine, sec-butylamine, tert-butylamine, n-pentylamine, sec-pentylamine, pentyl-3-amine, neopentylamine, n-hexylamine, 2-hexylamine, 3-hexylamine, isohexylamine, 1-methylpentylamine, 2-ethylbutyl-amine, 2-butylamine, 2-methylpentylamine, 1,1-dimethylbutylamine, 1,3-dimethylbutylamine, 3,3-dimethylbutylamine, 2-methyl-3-pentylamine, 3-methylpentylamine, 3-methyl-3-pentylamine, 3-methyl-2-pentylamine, 2-methylbutyl-1-amine, or 1,2,2-trimethyl-propylamine.

D30. In embodiment D30, the process of any one of embodiments D1 to D4, D5A and D7 is wherein the amine is cyclopropylamine, cyclobutylamine, cyclopentylamine, cyclohexylamine, 2-methylcyclopropylamine, 2-methylcyclopentylamine, 3-methylcyclopentyl-amine, or 2-ethylcyclopropylamine.

D31. In embodiment D31, the process of any one of embodiments D1 to D4, and D7B to D9 is wherein the amine is N-methylethylamine, diethylamine, N-methyl-n-propylamine, N-methylisopropylamine, N-allylmethylamine, N-methylpropargylamine, N-ethyl-n-propylamine, N-ethylisopropylamine, N-methylbutylamine, N-methyl-2-butylamine, N-tert-butyl-methyl-amine, N-methyl-cyclobutylamine, N-ethylcyclopropylamine, 1-cyclopropyl-N-methylmethanamine, N-ethyl-prop-2-yn-1-amine, N-ethylallylamine, N-methylpentylamine, N-methyl-2-pentylamine, N-methyl-3-pentylamine, N,3-dimethylbutane-2-amine, N,2-dimethylbutane-2-amine, N,3-dimethylbutane-2-amine, N-methylcyclopentylamine, N-ethyl-1-butylamine, N-ethyl-2-butylamine, N-ethyl-2-methyl-2-propylamine, N-ethyl-2-methylpropyl-amine, N-ethylcyclobutylamine, di-n-propylamine, di-isopropylamine, N-isopropylpropylamine, diallylamine, dipropargylamine, or allylpropargylamine. In one embodiment of B31, the amine is not diethylamine.

D32. In embodiment D32, the process of any one of embodiments D1 to D4, D7B and D8 is wherein the amine is N-methylethylamine, diethylamine, N-methyl-n-propylamine, N-methyl-isopropylamine, N-ethyl-n-propylamine, N-ethyl-isopropylamine, N-methylbutylamine, N-methyl-2-butylamine, N-tert-butyl-methyl-amine, N-methylpentyl-1-amine, N-methyl-2-pentylamine, N-methyl-3-pentylamine, N,3-dimethylbutane-2-amine, N,2-dimethylbutane-2-amine, N,3-dimethylbutane-2-amine, N-ethyl-1-butylamine, N-ethyl-2-butylamine, N-ethyl-2-methyl-2-propylamine, N-ethyl-2-methylpropylamine, di-n-propylamine, di-isopropylamine, or N-isopropylpropylamine. In one embodiment of B31, the amine is not diethylamine.

D33. In embodiment D33, the process of any one of embodiments D1 to D4, and D7B, and D9 is wherein the amine is N-methylcyclobutylamine, N-ethylcyclopropylamine, N-methylcyclopentylamine, or N-ethylcyclobutylamine.

D34. In embodiment D34, the process of any one of embodiments D1 to D4, and D11 is wherein the amine is azetidine, pyrrolidine, piperidine, piperazine, morpholine, azepane, or azocane.

D35. In embodiment D35, the process of any one of embodiments D1 to D3, D5, and D12 to D16, D19, D20, D22, D23, and D25, is wherein the amine is ethylenediamine, propane-1,3-diamine, butane-1,4-diamine, pentane-1,5-diamine, hexane-1,6-diamine, $N^1,N^2$-dimethyl-ethane-1,2-diamine, or $N^1,N^2$-diethylethane-1,2-diamine.

D36. In embodiment D36, the process of embodiment D1 to D3 is wherein the amine is N-methylethylamine, diethylamine, N-methyl-n-propylamine, N-methyl-isopropylamine, N-ethyl-n-propylamine, N-ethyl-isopropylamine, azetidine, pyrrolidine, piperidine, or morpholine.

D37. In embodiment D37, the process of embodiment D1 to D3, or D36, is wherein the amine is diethylamine. In one embodiment, the process of embodiment D37, is wherein the molar ratio of diethylamine to Compound 1 in the mixture is at least about 1:0.5. In another embodiment, the process of embodiment D37, is wherein the molar ratio of diethylamine to Compound 1 in the mixture is from 1:1 to about 10:1. In yet another embodiment, the process of embodiment D37, is wherein the molar ratio of diethylamine to Compound 1 in the mixture is from 1:1 to about 9:1. In yet another embodiment, the process of embodiment D37, is wherein the molar ratio of diethylamine to Compound 1 in the mixture is from 1:1 to about 8:1. In yet another embodiment, the process of embodiment D37, is wherein the molar ratio of diethylamine to Compound 1 in the mixture is from 3:1 to about 6:1. In yet another embodiment, the process of embodiment D37, is wherein the molar ratio of diethylamine to Compound 1 in the mixture is about 5:1. In yet another embodiment, the process of embodiment D37, is wherein the molar ratio of diethylamine to Compound 1 in the mixture is from 4:1 to about 6:1.

D38. In embodiment D38, the process of any one of embodiments D1 to D37, is wherein one or more anti-solvents are added to the mixture of Step (a1) to obtain a solid amine solvate of Compound 1.

D39. In embodiment D39, the process of any one of embodiments D1 to D37, is wherein one or more anti-solvents and a solid crystalline seed of Compound 1 and/or a solid crystalline seed of the amine solvate of Compound 1 are added to the mixture of Step (a1) to obtain a solid amine solvate of Compound 1.

D39A. In embodiment D39A, the process of any one of embodiments D1 to D39, is wherein the mixture of Step (a1) is a solution.

D40. In embodiment D40, the process of embodiment D38, D39, or D39A is wherein the one or more anti-solvents of Step (b1) are independently selected from alkanes and water. In a subembodiment of embodiment D40, the one or more anti-solvents are independently selected from the group consisting of water, n-heptane, n-hexane, isooctane, pentane, cyclohexane, and cyclopentane.

D41. In embodiment D41, the process of embodiment D38, D39, D39A, or D40, is wherein the anti-solvent in Step (b1) is n-heptane.

D42. In embodiment D42, the process of any one of embodiments D2 to D41, is wherein the one or more suitable organic solvents of Step (a1) are polar organic solvents independently selected from the group consisting of alcohols, ethers, toluene, ketones, esters, halogenated alkanes, nitromethane, N-methylpyrrolidinone, acetonitrile, dimethylformamide, and dimethylacetamide.

D42a. In embodiment D42a, the process of any one of embodiments D2 to D41, is wherein the one or more suitable organic solvents of Step (a1) are polar organic solvents independently selected from the group consisting of ethers, toluene, ketones, esters, halogenated alkanes, nitromethane, N-methylpyrrolidinone, acetonitrile, dimethylformamide, and dimethylacetamide.

D43. In embodiment D43, the process of embodiment any one of embodiments D2 to D42, is wherein the one or more suitable organic solvents of Step (a1) are independently selected from the group consisting of methanol, ethanol, n-propanol, isopropanol, n-butanol, 1,2-propanediol, methylene dichloride, chloroform, 1,2-dichloroethane, diethyl ether, diisopropyl ether, methyl tert-butyl ether (MTBE), methyl tert-amyl ether, methyl acetate (MeOAc), ethyl acetate (EtOAc), n-propylacetate, isopropylacetate (IPAc), butyl acetate, n-methyl pyrrolidinone (NMP), dimethyl formamide (DMF), dimethylacetamide (DMAc), tetrahydrofuran (THF), 2-methyl THF (2-MeTHF), dimethoxyethane (DME), toluene, acetone, methyl ethyl ketone (MEK), nitromethane, acetonitrile (ACN), and 1,4-dioxane.

D43a. In embodiment D43a, the process of embodiment any one of embodiments D2 to D42, is wherein the one or more suitable organic solvents of Step (a1) are independently selected from the group consisting of methanol, n-propanol, isopropanol, n-butanol, 1,2-propanediol, methylene dichloride, chloroform, 1,2-dichloroethane, diethyl ether, diisopropyl ether, methyl tert-butyl ether (MTBE), methyl tert-amyl ether, methyl acetate (MeOAc), ethyl acetate (EtOAc), n-propylacetate, isopropylacetate (IPAc), butyl acetate, n-methyl pyrrolidinone (NMP), dimethyl formamide (DMF), dimethylacetamide (DMAc), tetrahydrofuran (THF), 2-methyl THF (2-MeTHF), dimethoxyethane (DME), toluene, acetone, methyl ethyl ketone (MEK), nitromethane, acetonitrile (ACN), and 1,4-dioxane.

D43b. In embodiment D43b, the amine solvate of embodiment D43a, is wherein the one or more suitable organic solvents are independently selected from methylene dichloride, chloroform, 1,2-dichloroethane, diethyl ether, diisopropyl ether, methyl tert-butyl ether (MTBE), methyl tert-amyl ether, methyl acetate (MeOAc), ethyl acetate (EtOAc), n-propylacetate, isopropylacetate (IPAc), butyl acetate, n-methyl pyrrolidinone (NMP), dimethyl formamide (DMF), dimethylacetamide (DMAC), tetrahydrofuran (THF), 2-methyl THF (2-MeTHF), dimethoxyethane (DME), toluene, acetone, methyl ethyl ketone (MEK), nitromethane, acetonitrile (ACN), and 1,4-dioxane.

D44. In embodiment D44, the process of embodiments D42 to D43b, is wherein the suitable organic solvent of Step (a1) is MTBE.

D45. In embodiment D45, the process of any one of embodiments D37 to D44, is wherein the diethylamine solvate of Compound 1 is a crystalline solid.

D46. In embodiment D46, the process of embodiment D45, is wherein the diethylamine solvate of Compound 1 is crystalline Form B polymorph having an X-ray powder diffraction pattern as described in the Summary.

D47-D54. In embodiments D47 to D54, the process of embodiment D46, is wherein the crystalline Form B has an X-ray powder diffraction pattern as described in any one of above embodiments C2 to C9, respectively.

D55. In embodiment D55, the process of any one of embodiments D1 to D54, is wherein the amine solvate of Compound 1 is converted to Compound 1.

D56. In embodiment D56, the process of any one of embodiments D1 to D55, is wherein the amine solvate of Compound 1 is converted to Compound 1 by heating the amine solvate to remove the amine from the amine solvate.

D57. In embodiment D57, the process of any one of embodiments D1 to D55, is wherein the amine solvent of Compound 1 is converted to Compound 1 by partitioning the amine solvate between one or more suitable organic solvents and an aqueous acidic solution.

D58. In embodiment D58, the process of embodiment D57, is wherein the one or more suitable organic solvents containing Compound 1 is isolated and concentrated to provide a solid form of Compound 1.

D59. In embodiment D59, the process of embodiment D56 or D58, is wherein the crystalline Form A polymorph Compound 1 has an X-ray powder diffraction pattern as described in the Summary is produced.

D60-D69. In embodiment D60 to D69, the process of embodiment D59, is wherein crystalline Form A polymorph of Compound 1 has an X-ray powder diffraction pattern as described in above embodiments A2 to A11, respectively, is produced.

D70. In embodiment D70, the process of any one of embodiments D1 to D69, further comprises preparing the Compound 1 of Step (a1), comprising:
  (a) treating 3-fluoro-5-(((1R,2aR)-3,3,4,4-tetrafluoro-1,2a-dihydroxy-2,2a,3,4-tetrahydro-1H-cyclopenta[cd]inden-7-yl)oxy)benzonitrile with a deoxyfluorinating agent with or without a base, in a suitable organic solvent and optionally in the presence of triethylamine trihydrofluoride ($Et_3N \cdot 3HF$) and
  (b) purifying the mixture from Step (a) to obtain Compound 1.

D71. In embodiment D71, the process of embodiment D70, is wherein the deoxyfluorinating agent is pyridine-2-sulfonyl fluoride, PBSF, bis(2-methoxyethylamino)sulfur trifluoride (BAST), or (diethylamino)sulfur trifluoride (DAST).

D72. In embodiment D72, the process of embodiment D70 or D71, is wherein the organic base is (tert-butylimino)tris-(pyrrolidino)phosphorane (BTPP), 2-tert-butyl-1,1,3,3-tetramethyl-guanidine (BTMG). 1,8-diazabicyclo-[5.4.0]undec-7-ene, or 7-methyl-1,5,7-triaza-bicyclo-[4.4.0]dec-1-ene (DBU).

D73A. In embodiment D73A, the process of embodiment D70, D71 or D72, is wherein the deoxyfluorinating agent is PBSF or BAST.

D73. In embodiment D73, the process of embodiment D70, D71 or D72, is wherein the deoxyfluorinating agent is PBSF, the organic base is BTMG or BTPP and $Et_3N \cdot 3HF$ is present.

D74. In embodiment D74, the process of any one of embodiments D70 to D73, is wherein the one or more suitable organic solvents are selected from ethers, esters, ketones, haloalkanes, acetates, toluene, and xylene.

D75. In embodiment D75, the process of any one of embodiments D70 to D74, is wherein the one or more suitable organic solvents are selected from dichloromethane, MTBE, IPAc, tetrahydrofuran, 2-methyl-tetrahydrofuran, ethyl acetate, and toluene.

D76. In embodiment D76, the process of any one of embodiments D70 to D75, is wherein the suitable organic solvent is 2-methyltetrahydrofran.

D77. In embodiment D77, the process of any one of embodiments D73 to D76, is wherein the reaction is carried out from about −20° C. to about room temperature.

D78. In embodiment D78, the process of any one of embodiments D73 to D77, is wherein the reaction is carried out at about −20° C.

D79. In embodiment D79, the process of any one of embodiments D73 to D78, is wherein the molar ratio of BTPP or BTMG:$Et_3N \cdot 3HF$ is from about 6:1 to about 1:1.

D80. In embodiment D80, the process of any one of embodiments D73 to D79, is wherein the molar ratio of BTPP or BTMG:Et$_3$N·3HF is from about 6:1 to about 3:1.

D81. In embodiment D81, the process of any one of embodiments D73 to D79, is wherein the molar ratio of BTMG:Et$_3$N·3HF is about 5:1.

D82. In embodiment D82, the process of any one of embodiments D73 to D81, is wherein the molar ratio of PBSF:Et$_3$N·3HF is from about 8:1 to about 1.7:1.

D83. In embodiment D83, the process of any one of embodiments D73 to D82, is wherein the molar ratio of PBSF:Et$_3$N·3HF is about 8:1, about 5:1, about 3:1 or about 1.7:1.

D84. In embodiment D84, the process of any one of embodiments D73 to D83, is wherein the molar ratio of PBSF:Et$_3$N·3HF is about 3:1.

D85. In embodiment D85, the process of embodiment D70, 71, or D72, is wherein the deoxyfluorinating agent is pyridine-2-sulfonyl fluoride and the base is 1,8-diazabicyclo-[5.4.0]undec-7-ene or 7-methyl-1,5,7-triaza-bicyclo-[4.4.0]dec-1-ene.

D86. In embodiment D86, the process of embodiment D70, D71 or D85, is wherein the suitable organic solvent is tetrahydrofuran.

Embodiment E

E1. In embodiment E1, provided is a process of preparing crystalline Form B polymorph of a diethylamine solvate of Compound 1 having an X-ray powder diffraction pattern as described in the third aspect of the Summary or any one of embodiments C2 to C9.

E2. In embodiment E2, the process of embodiment E1, is wherein Compound 1 is contacted with diethylamine by adding Compound 1 to the diethylamine or by adding the diethylamine to a mixture of Compound 1 in one or more suitable organic solvents in Step (a2).

E3. In embodiment E3, the process of embodiment E1, is wherein the diethylamine is added to the mixture of Compound 1 in one or more suitable organic solvents in Step (a2). In one embodiment, the process of embodiment E3, is wherein the molar ratio of diethylamine to Compound 1 in the mixture is at least about 1:0.5. In another embodiment, the process of embodiment E3, is wherein the molar ratio of diethylamine to Compound 1 in the mixture is from 1:1 to about 10:1. In yet another embodiment, the process of embodiment E3, is wherein the molar ratio of diethylamine to Compound 1 in the mixture is from 1:1 to about 9:1. In yet another embodiment, the process of embodiment E3, is wherein the molar ratio of diethylamine to Compound 1 in the mixture is from 1:1 to about 8:1. In yet another embodiment, the process of embodiment E3, is wherein the molar ratio of diethylamine to Compound 1 in the mixture is from 3:1 to about 6:1. In yet another embodiment, the process of embodiment E3, is wherein the molar ratio of diethylamine to Compound 1 in the mixture is about 5:1. In yet another embodiment, the process of embodiment E3, is wherein the molar ratio of diethylamine to Compound 1 in the mixture is from 4:1 to about 6:1. In yet another embodiment, the process of embodiment E3, is wherein the molar ratio of diethylamine to Compound 1 in the mixture is from about 1 or greater than 1.

E4. In embodiment E4, the process of any one of embodiments E1 to E3, is wherein one or more anti-solvents are added to the mixture of Step (a2) to obtain crystalline Form B polymorph of the diethylamine solvate of Compound 1.

E5. In embodiment E5, the process of any one of embodiments E1 to E3, is wherein one or more anti-solvents and a solid crystalline seed of Compound 1 and/or a solid crystalline seed of the diethylamine solvate of Compound 1 are added to the mixture of Step (a2) to obtain crystalline Form B polymorph of the diethylamine solvate of Compound 1.

E5A. In embodiment E5A, the process of any one of embodiments E1 to E5, is wherein the mixture of Step (a2) is a solution.

E6. In embodiment E6, the process of any one of embodiments E1 to E5A, is wherein the one or more anti-solvents in Step (b2) are independently selected from alkanes and water. In a subembodiment of embodiment E6, the one or more anti-solvents are independently selected from the group consisting of water, n-heptane, n-hexane, isooctane, pentane, cyclohexane, and cyclopentane.

E7. In embodiment E7, the process of any one of embodiments E1 to E6, is wherein the anti-solvent in Step (b2) is n-heptane.

E8. In embodiment E8, the process of any one of embodiments E1 to E7, is wherein the one or more suitable organic solvents of Step (a2) are polar organic solvents independently selected from the group consisting of alcohols, ethers, toluene, ketones, esters, halogenated alkanes, nitromethane, N-methylpyrrolidinone, acetonitrile, dimethylacetamide, and dimethylformamide.

E8a. In embodiment E8a, the process of any one of embodiments E1 to E7, is wherein the one or more suitable organic solvents of Step (a2) are polar organic solvents independently selected from the group consisting of ethers, toluene, ketones, esters, halogenated alkanes, nitromethane, N-methylpyrrolidinone, acetonitrile, dimethylacetamide, and dimethylformamide.

E9. In embodiment E9, the process of embodiment any one of embodiments E1 to E7, is wherein the one or more suitable organic solvents of Step (a2) are independently selected from the group consisting of methanol, ethanol, n-propanol, isopropanol, n-butanol, 1,2-propanediol, methylene dichloride, chloroform, 1,2-dichloroethane, diethyl ether, diisopropyl ether, methyl tert-butyl ether (MTBE), methyl tert-amyl ether, methyl acetate (MeOAc), ethyl acetate (EtOAc), n-propylacetate, isopropylacetate (IPAc), butyl acetate, n-methyl pyrrolidinone (NMP), dimethyl formamide (DMF), dimethylacetamide (DMAc), etrahydrofuran (THF), 2-methyl THF (2-MeTHF), dimethoxyethane (DME), toluene, acetone, methyl ethyl ketone (MEK), nitromethane, acetonitrile (ACN), and 1,4-dioxane.

E9a. In embodiment E9a, the process of embodiment any one of embodiments E1 to E7, is wherein the one or more suitable organic solvents of Step (a2) are independently selected from the group consisting of methanol, n-propanol, isopropanol, n-butanol, 1,2-propanediol, methylene dichloride, chloroform, 1,2-dichloroethane, diethyl ether, diisopropyl ether, methyl tert-butyl ether (MTBE), methyl tert-amyl ether, methyl acetate (MeOAc), ethyl acetate (EtOAc), n-propylacetate, isopropylacetate (IPAc), butyl acetate, n-methyl pyrrolidinone (NMP), dimethyl formamide (DMF), dimethylacetamide (DMAc), tetrahydrofuran (THF), 2-methyl THF (2-MeTHF), dimethoxyethane (DME), toluene, acetone, methyl ethyl ketone (MEK), nitromethane, acetonitrile (ACN), and 1,4-dioxane.

E9b. In embodiment E9b, the process of embodiment any one of embodiments E1 to E7, is wherein the one or more suitable organic solvents of Step (a2) are independently selected from the group consisting of methylene dichloride, chloroform, 1,2-dichloroethane, diethyl ether, diisopropyl ether, methyl tert-butyl ether (MTBE), methyl tert-amyl ether, methyl acetate (MeOAc), ethyl acetate (EtOAc), n-propylacetate, isopropylacetate (IPAc), butyl acetate, n-methyl pyrrolidinone (NMP), dimethyl formamide (DMF), dimethylacetamide (DMAc), tetrahydrofuran (THF), 2-methyl THF (2-MeTHF), dimethoxyethane (DME), toluene, acetone, methyl ethyl ketone (MEK), nitromethane, acetonitrile (ACN), and 1,4-dioxane.

E10. In embodiment D10, the process of embodiment E9, E9a, or E9b, is wherein the suitable organic solvent is MTBE.

E11. In embodiment E11, the process of any one of embodiments E1 to E10, is wherein the diethylamine of solvate Compound 1 is optionally converted to Compound 1 by heating the diethylamine solvate of Compound 1 to remove the diethylamine from the diethylamine solvate of Compound 1.

E12. In embodiment E12, the process of any one of embodiments E1 to E10, is wherein the diethylamine of solvate Compound 1 is optionally converted to Compound 1 by partitioning the diethylamine solvate of Compound 1 between one or more suitable organic solvent and an aqueous acidic solution. In one embodiment, the acid is hydrochloric acid.

E13. In embodiment E13, the process of embodiment E12, is wherein the one or more organic solvents containing Compound 1 is isolated and concentrated to provide a solid form of Compound 1.

E14 to E24. In embodiments E14 to E24, the process of any one of embodiments E11 to E13, is wherein Compound 1 is a crystalline Form A polymorph of Compound 1 having an X-ray powder diffraction pattern as defined in any one of Embodiments A1 to A11, respectively, is produced.

Embodiment F

F1. In embodiment F1, provided is a process of preparing crystalline Form A polymorph of Compound 1 from a diethylamine solvate of Compound 1 as described in the sixth aspect of the Summary or a composition of any one of Embodiment I1 to I7A below.

F2 to F10. In embodiments F2 to F10, the process of embodiment F1, is wherein the diethylamine solvate of Compound 1 of the third aspect of the Summary is crystalline Form B polymorph having an X-ray powder diffraction pattern as described in above embodiments C1 to C9, respectively.

F11. In embodiment F11, the process of any one of embodiments F1 to F10, is wherein the diethylamine is removed from the diethylamine solvate of Compound 1 by heating the diethylamine solvate of Compound 1 or a composition of any one of Embodiment I1 to I7A below.

F12. In embodiment F12, the process of any one of embodiments F1 to F11, is wherein the diethylamine is removed from the diethylamine solvate of Compound 1 by partitioning the diethylamine solvate of Compound 1 or a composition of any one of Embodiment I1 to I7A below between one or more suitable organic solvent and an aqueous acidic solution. In one embodiment the acid is hydrochloric acid and the solvent is MTBE.

F13 to F24. In embodiment F13, the process of embodiment F12, is wherein the one or more suitable organic solvents, including MTBE, are isolated and concentrated to provide crystalline Form A polymorph of Compound 1 having an X-ray powder diffraction pattern as described in any one of embodiments A1 to A11 above, respectively.

F25. In embodiment F25, the process of any one of embodiments F1 to F24, is wherein the crystalline Form A polymorph of Compound 1 is recrystallized from one or more suitable organic solvents.

F26. In embodiment F26, the process of embodiment F25, is wherein the crystalline Form A polymorph of Compound 1 is dissolved in one or more suitable organic solvents independently selected from the group consisting of alcohols, ethers, toluene, ketones, esters, halogenated alkanes, nitromethane, N-methylpyrrolidinone, acetonitrile, dimethylacetamide and dimethylformamide.

F27. In embodiment F27, the process of embodiment F26, is wherein the one or more suitable organic solvents are selected from the group consisting methanol, ethanol, n-propanol, isopropanol, n-butanol, 1,2-propanediol, methylene dichloride, chloroform, 1,2-dichloroethane, diethyl ether, diisopropyl ether, methyl tert-butyl ether (MTBE), methyl tert-amyl ether, methyl acetate (MeOAc), ethyl acetate (EtOAc), n-propylacetate, isopropylacetate (IPAc), butyl acetate, n-methyl pyrrolidinone (NMP), dimethyl formamide (DMF), dimethylacetamide (DMAc), tetrahydrofuran (THF), 2-methyl THF (2-MeTHF), dimethoxyethane (DME), toluene, acetone, methyl ethyl ketone (MEK), nitromethane, acetonitrile (ACN), and 1,4-dioxane. In an embodiment the suitable organic solvent is isopropyl acetate.

F28. In embodiment F28, the process of embodiment F26 or F27, is wherein one or more anti-solvents and/or solid crystalline seed of Compound 1 are added.

F29. In embodiment F29, the process of embodiment F28, is wherein the one or more anti-solvents are independently selected from alkanes and water.

F30. In embodiment F30, the process of embodiment F29, is wherein the one or more anti-solvents are independently selected from the group consisting of water, n-heptane, n-hexane, isooctane, pentane, cyclohexane, and cyclopentane.

F31. In embodiment F31, the process of embodiment F30, is wherein the anti-solvent is n-heptane.

Embodiment G

G1. In embodiment G1, provided is a process of making crystalline Form A polymorph of Compound 1 having an X-ray powder diffraction pattern as described in the seventh aspect of the Summary.

G2. In embodiment G2, the process of embodiment G1, is wherein one or more anti-solvents are added to a solution of Compound 1 in one or more suitable organic solvents independently selected from the group consisting of alcohols, ethers, toluene, ketones, esters, halogenated alkanes, nitromethane, N-methylpyrrolidinone, acetonitrile, dimethylacetamide and dimethylformamide.

G3. In embodiment G3, the process of embodiment G2 is wherein the one or more suitable organic solvents are selected from the group consisting methanol, ethanol, n-propanol, isopropanol, n-butanol, 1,2-propanediol, methylene dichloride, chloroform, 1,2-dichloroethane, diethyl ether, diisopropyl ether, methyl tert-butyl ether (MTBE), methyl tert-amyl ether, methyl acetate (MeOAc), ethyl acetate (EtOAc), n-propylacetate, isopropylacetate (IPAc), butyl acetate, n-methyl pyrrolidinone (NMP), dimethyl formamide (DMF), dimethylacetamide (DMAc), tetrahydrofuran (THF), 2-methyl THF (2-MeTHF), dimethoxyethane (DME), toluene, acetone, methyl ethyl ketone (MEK), nitromethane, acetonitrile (ACN), and 1,4-dioxane. In an embodiment the suitable organic solvent is isopropyl acetate.

G4. In embodiment G4, the process of embodiment G2 or G3, is wherein one or more anti-solvents is added.

G5. In embodiment G5, the process of embodiment G4, is wherein the one or more anti-solvents is independently selected from alkanes and water.

G6. In embodiment G6, the process of embodiment G5, is wherein the one or more anti-solvents is independently selected from the group consisting of water, n-heptane, n-hexane, isooctane, pentane, cyclohexane, and cyclopentane.

G7. In embodiment G7, the process of embodiment G6, is wherein the anti-solvent is n-heptane.

G8. In embodiment G8, the process of any one of embodiments G1 to G7, is wherein the process is carried out at about 0° C. to about 70° C.

Embodiment H

H1. In embodiment H1, provided is a process of making Compound 1 as described in the eighth aspect of the Summary.

H2. In embodiment H2, the process of embodiment H1, is wherein the organic base in Step (a5) is (tert-butylimino)tris-(pyrrolidino)phosphorane (BTPP) or 2-tert-butyl-1,1,3,3-tetramethyl-guanidine (BTMG).

H3. In embodiment H3, the process of embodiment H1 or H2, is wherein the organic base in Step (a5) is BTMG.

H4. In embodiment H4, the process of any one of embodiments H1 to H3, is wherein the one or more suitable organic solvents in Step (a5) are selected from ethers, esters, haloalkanes, ketones, acetates, toluene, and xylene.

H5. In embodiment H5, the process of any one of embodiments H1 to H4, is wherein the one or more suitable organic solvents in Step (a5) are selected from tetrahydrofuran, 2-methyl-tetrahydrofuran, ethyl acetate, IPAc, MTBE, methylene chloride, or toluene.

H6. In embodiment H6, the process of any one of embodiments H1 to H5, is wherein the suitable organic solvent in Step (a5) is 2-methyltetrahydrofuran.

H7. In embodiment H7, the process of any one of embodiments H1 to H6, is wherein the reaction of Step (a5) is carried out from about −20° C. to about room temperature.

H8. In embodiment H8, the process of any one of embodiments H1 to H7, is wherein the reaction of Step (a5) is carried out at about −20° C.

H9. In embodiment H9, the process of any one of embodiments H1 to H8, is wherein the molar ratio of BTPP or BTMG:Et$_3$N·3HF in Step (a5) is from about 6:1 to about 1:1.

H10. In embodiment H10, the process of any one of embodiments H1 to H9, is wherein the molar ratio of BTPP or BTMG:Et$_3$N·3HF in Step (a5) is from about 6:1 to about 3:1.

H11. In embodiment H11, the process of any one of embodiments H1 to H9, is wherein the molar ratio of BTMG:Et$_3$N·3HF in Step (a5) is about 5:1.

H12. In embodiment H12, the process of any one of embodiments H1 to H11, is wherein the molar ratio of PBSF:Et$_3$N·3HF in Step (a5) is from about 8:1 to about 1.7:1.

H13. In embodiment H13, the process of any one of embodiments H1 to H12, is wherein the molar ratio of PBSF:Et$_3$N·3HF in Step (a5) is about 8:1, about 5:1, about 3:1 or about 1.7:1.

H14. In embodiment H14, the process of any one of embodiments H1 to H13, is wherein the molar ratio of PBSF:Et$_3$N·3HF in Step (a5) is about 3:1.

H15 to H68. In embodiment H15-68, the process of any one of embodiments H1 to H14, is wherein Compound 1 is converted in Step (c5) to an amine solvate of Compound 1 by the process described above in embodiments D1 to D54, respectively.

H70-H72. In embodiment H70-72, the process of any one of embodiments H15 to H68, is wherein the amine solvate of Compound 1 is converted to Compound 1 by the process described in above embodiments D56 to D58, respectively.

H73-H83. In embodiment H73-83, the process of any one of embodiments H70 or H72, is wherein the Compound 1 is a crystalline Form A polymorph as described in above embodiments A1 to A11, respectively.

Embodiment I

I1. In embodiment I1, provided is a solid composition as described in the ninth aspect of the Summary. The % weight ratio is calculated as follows: (% weight of a diethylamine solvate of Compound 1)/the total of {(% weight of Compound 1) and [% weight of (a diethylamine solvate of Compound 1)]}. In a sub-embodiment of embodiment I1, the % weight is determined by HPLC.

I2. In embodiment I2, the solid composition of embodiment I1, is wherein the % weight ratio of the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile to 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile in the composition is about 1 to 4 (or less), 1 to 3 (or less), 1 to 2 (or less), 1 to 1 (or less), or 1 to 0.25 (or less). In a sub-embodiment, the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile is a crystalline Form B polymorph of any one of embodiments C1 to C9.

I2A. In embodiment I2A, the solid composition of embodiment I1, is wherein the % weight ratio of the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile to 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile in the composition is from about 1:4, 1:3, 1:2; 1:1, or 1:0.25 to about 1:0.001. In a sub-embodiment, the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile is a crystalline Form B polymorph of any one of embodiments C1 to C9.

I3. In embodiment I3, the solid composition of embodiment I1, is wherein the % weight ratio of the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile to 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile in the composition is about 1 to 0.1 (or less). In a sub-embodiment, the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile is a crystalline Form B polymorph of any one of embodiments C1 to C9.

I3A. In embodiment I3A, the solid composition of embodiment I1, is wherein the % weight ratio of the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile to 3-fluoro-5-(((1S,2aR)-1,3,3,4,4-pentafluoro-2a-hydroxy-2,2a,3,4-tetrahydro-1H- cyclopenta[cd]inden-7-yl)oxy)benzonitrile in the composition is from about 1:0.1 to about 1:0.001. In a sub-embodiment, the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile is a crystalline Form B polymorph of any one of embodiments C1 to C9.

I4. In embodiment I4, the solid composition of embodiment I1, is wherein the % weight ratio of the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile to 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile in the composition is about 1 to 0.05 (or less). In a sub-embodiment, the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile is a crystalline Form B polymorph of any one of embodiments C1 to C9.

I4A. In embodiment I4A, the solid composition of embodiment I1, is wherein the % weight ratio of the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile to 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile in the composition is from about 1:0.05 to about 1:0.001. In a sub-embodiment, the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile is a crystalline Form B polymorph of any one of embodiments C1 to C9.

I5. In embodiment I5, the solid composition of embodiment I1, is wherein the % weight ratio of the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile to 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile in the composition is about 1 to 0.03 (or less). In a sub-embodiment, the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile is a crystalline Form B polymorph of any one of embodiments C1 to C9.

I5A. In embodiment I5A, the solid composition of embodiment I1, is wherein the % weight ratio of the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile to 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile in the composition is from about 1:0.03 to about 1:0.001. In a sub-embodiment, the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile is a crystalline Form B polymorph of any one of embodiments C1 to C9.

I6. In embodiment I6, the solid composition of embodiment I1, is wherein the % weight ratio of the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile to 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile in the composition is about 1 to 0.02 (or less). In a sub-embodiment, the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile is a crystalline Form B polymorph of any one of embodiments C1 to C9.

I6A. In embodiment I6A, the solid composition of embodiment I1, is wherein the % weight ratio of the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile to 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile in the composition is from about 1:0.02 to about 1:0.001. In a sub-embodiment, the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile is a crystalline Form B polymorph of any one of embodiments C1 to C9.

I7. In embodiment I7, the solid composition of embodiment I1, is wherein the % weight ratio of the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile to 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile in the composition is about 1 to 0.01 (or less). In a sub-embodiment, the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile is a crystalline Form B polymorph of any one of embodiments C1 to C9.

I7A. In embodiment I7A, the solid composition of embodiment I1, is wherein the % weight ratio of the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile to 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile in the composition is from about 1:0.01 to about 1:0.001. In a sub-embodiment, the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile is a crystalline Form B polymorph of any one of embodiments C1 to C9.

In embodiments above, reference to an embodiment, includes subembodiments thereof. For example, reference to embodiment D31, includes combination with the embodiment(s) contained therein.

Utility

Compound 1 is useful for the treatment of HIF-2α mediated diseases, which include but are not limited to, various types of cancer, liver disease such as nonalcoholic steatohepatitis (NASH), inflammatory disease such as inflammatory bowel disease (IBD), pulmonary diseases such as pulmonary arterial hypertension (PAH), and iron load disorders.

HIF-2α plays an important role in the initiation and progression of many human cancers. Many extensive studies have demonstrated the critical role of increased HIF-2α activity in driving clear cell renal cell carcinoma (ccRCC) (see review by Shen and Kaelin, Seminars in Cancer Biology 23: 18-25, 2013). Abnormal HIF-2α activity is largely due to loss of function of a tumor suppressor, VHL. It is known that over eighty percent of ccRCC have defective VHL either through deletion, mutation or disturbed post-translational modification. Defective VHL leads to constitutively active HIF-α proteins regardless of oxygen level. Various studies employing gain-of-function and loss-of-function approaches in mouse models have demonstrated that HIF-2α is the key oncogenic substrate of VHL (see Kondo, et al. Cancer Cell 1: 237-246, 2002; Kondo, et al. PLoS Biology 1: 439-444, 2002; Maranchi, et al. Cancer Cell 1: 247-255, 2002; Zimmer, et al. Mol. Cancer Res 2: 89-95, 2004). For example, knockdown of HIF-2α in VHL-null tumors inhibited tumor formation; while reintroduction of VHL and overexpression of HIF-2α overcame the tumor suppressive role of VHL. Moreover, single nucleotide polymorphism in HIF-2α, is associated with resistant to PHD-mediated degradation, has been linked to an increased risk of developing RCC. In addition to serving as an archetypical tumor-initiating event in ccRCC, the VHL-HIF-2α axis has also been implicated in ccRCC tumor metastasis through its downstream CXCR4 and CYTIP (see Vanharanta et al. Nature Medicine 19: 50-59, 2013; Peter Staller et al. Nature. 2003 Sep. 18; 425(6955):307-11). Taken together, these studies strongly support the potential therapeutic utility of HIF-2α targeted agents for the treatment of ccRCC.

Defective VHL not only predisposes patients to kidney cancer (with a70% lifetime risk), but also to hemangioblastomas, pheochromocytoma, endolymphatic sac tumors, and pancreatic neuroendocrine tumors. Tumors derived from defective VHL are frequently driven by the constitutively active downstream HIF-α, proteins, with the majority of these dependent on HIF-2α activity (see Maher, et al. Eur. J. Hum. Genet. 19: 617-623, 2011). Both genetic and epigenetic mechanisms can lead to the loss of function in VHL. Epigenetic inactivation of VHL expression and thus constitutive activation of HIF-α proteins has been found in many cancers including RCC, multiple myeloma, retinoblastoma, NSCLC, pancreatic endocrine tumors, squamous cell carcinoma, acute myeloid leukemia, myelodysplastic syndrome, and esophageal squamous cell carcinoma (see reviewed in Nguyen, et al. Arch. Phann. Res 36: 252-263, 2013). HIF-2α has also been linked to cancers of the retina, adrenal gland and pancreas through both loss of function in VHL and activating mutations in HIF-2α. Recently, gain-of-function HIF-2α mutations have been identified in erythrocytosis and paraganglioma with polycythemia (see Zhuang, et al. NEJM 367: 922-930, 2012; Percy, et al. NEJM 358: 162-168, 2008; and Percy, et al. Am. J. Hematol. 87: 439-442, 2012). Notably, many of the known HIF-2α target gene products (e.g., VEGF, PDGF, and cyclin D1) have been demonstrated to play pivotal roles in cancers derived from kidney, liver, colon, lung, and brain. Thus, a HIF-2α targeted therapy could be beneficial for the above cancers when driven by these signaling events downstream of abnormal HIF-2α pathway activation. In addition to loss of function in VHL and activating mutation of HIF-2α, HIF-α, proteins are also frequently upregulated in the intratumor environment of rapidly growing tumors, due to the hypoxic condition resulting from poor vascularization in large tumors. The activated HIF-α pathways, in turn, further promotes tumor cell survival and proliferation by transcriptionally upregulating various essential factors.

A large body of studies have demonstrated a correlation between HIF-2α overexpression and poor prognosis in various cancers including cancers of astrocytoma, breast, cervical, colorectal, glioblastoma, glioma, head and neck, liver, non-small cell lung, melanoma, neuroblastoma, ovarian, and prostate, thereby supporting the pursuit of HIF-2α as a therapeutic target in treating these cancers (see reviewed in Keith, et al. Nature Rev. Cancer 12: 9-22, 2012). HIF-2α has been demonstrated to augment the growth of APC mutant colorectal cancer through its regulation of genes involved in proliferation, iron utilization and inflammation (see Xue, et al. Cancer Res 72: 2285-2293, 2012; and Xue and Shah, Carcinogenesis 32: 163-169, 2013). In hepatocellular carcinoma (HCC), knock-down of HIF-2α in preclinical models led to the inhibition of cell proliferation in vitro and tumor growth in vivo through the downregulation of VEGF and cyclin D 1 (see He, et al. Cancer Sci. 103: 528-534, 2012). In NSCLC, around 50% of patients exhibited overexpression of HIF-2α protein, which strongly correlates with higher VEGF expression and more importantly, reduced overall survival. Interestingly, HIF-1a does not correlate with reduced overall survival in lung cancer patients even though its expression is also often increased (see Giatromanolaki, et al. Br. J. Cancer 85: 881-890, 2001). Extensive studies in mice engineered with both non-degradable HIF-2α and mutant KRAS tumors have demonstrated an increased tumor burden and a decreased survival when compared to mice with only mutant KRAS expression (see Kim, et al. J. Clin. Invest. 119: 2160-2170, 2009). These studies demonstrate that HIF-2α promotes tumor growth and progression in lung cancer, and also negatively correlates with clinical prognosis.

HIF-2αs activity has been linked to the progression of chronic obstructive pulmonary disease (COPD), in addition to lung cancer, in mouse models (see Karoor, et al. Cancer Prev. Res. 5: 1061-1071, 2012). HIF-2α activity has also been demonstrated to be important in cancers of the central nervous system (see Holmquist-Mengelbier, et al. Cancer Cell 10: 413-423, 2006 and Li, et al. Cancer Cell 15: 501-513, 2009). HIF-2α knockdown reduced tumor growth in preclinical animal models of neuroblastoma, Conversely, increased level of HIF-2α correlated with advanced disease, poor prognosis and higher VEGF levels, which likely contribute to the poor clinical outcome. Similarly, higher HIF-2α expression has been correlated with a poor survival in glioma. Experimentally, inhibition of HIF-2α in glioma stem cells reduced cell proliferation and survival in vitro and tumor initiation in vivo. While HIF-1α is expressed in both neural progenitors and brain tumor stem cells, HIF-2α is found exclusively in the latter. Moreover, survival of glioma patients correlates to with HIF-2α, but not HIF-1α level.

One of downstream HIF-2α effector is cyclin D, an essential partner for the activation of CDK4 and CDK6. Therefore, administration of a HIF-2α inhibitor with CDK4/6 inhibitors, including abemaciclib (Verzenio®), palbociclib (Ibrance®) and ribociclib (Kisqali®) should result in downregulation of cyclin D, thereby increasing antiproliferative effects of CDK4/6 inhibitors. A recent study (Nicholson et al Sci Signal. 2019 Oct. 1; 12(601)) suggests that the antiproliferative effects of CDK4/6 inhibition were synergistic with HIF-2α inhibition in HIF-2α-dependent VHL-/- ccRCC cells.

Radiation therapy is frequently used for approximately 50% of cancer patients, either alone or in combination with other therapies. However, the hypoxia microenvironment within the tumor has long been associated with resistance to radiation therapy. Bhatt and co-workers found that decreased level of HIF-2α leads to increased sensitivity to ionizing radiation in renal cell carcinoma cell lines (see Bhatt, et al. BJU Int. 102: 358-363, 2008). Furthermore, mechanistic studies from Bertout et. al, have demonstrated that HIF-2α inhibition enhances the effectiveness of radiation through increased p53-dependent apoptosis (see Bertout, et al. PNAS 106: 14391-14396, 2009). Thus, HIF-2α targeted therapy could improve the response to radiation therapy in various cancers.

Somatostatinomas are somatostatin-producing neuroendocrine tumors that are rare, but often malignant. It has been found that HIF-2α mutations lead to the disruption of the prolyl hydroxylation domain (PHD) of HIF-2α, thus abolish the modification by PHDs, and subsequently reduce HIF-2α degradation mediated by VHL (see Yang, et al. Blood. 121: 2563-2566, 2013). The stabilized HIF-2α can then translocate to the nucleus, driving increased expression of hypoxia-related genes to contribute to somatostatinoma. Thus, a HIF-2α inhibitor will provide an alternative approach in treating somatostatinoma.

Polycythaemia is a hematologic disorder characterized by elevated hematocrit (the volume percentage of red blood cells in the blood), also known as erythrocytosis. Gain-of-function mutations in HIF-2α are associated with autosomal dominant erythrocytosis (see Percy, et al. N. Engl. J. Med. 358: 162-8, 2008 and Wilson et al. Case Rep Hematol. 6373706, 2016). In addition, mutations in PHD of HIF-2α, which is responsible in signaling HIF-2α for ubiquitination and degradation by VHL, have also been found to drive polycythaemia. Thus, inhibiting HIF-2α n, which is stabilized either by gain of function HIF-2α mutations or by loss of function mutations in PHD, VHL, by an HIF-2α inhibitor should be able to suppress HIF-2α downstream genes, such as EPO and thereby reducing hematocrit of polycythaemia.

Pheochromocytomas and paragangliomas (PPGLs) are rare neuroendocrine tumors that often develop on a background of predisposing genetic mutations, including loss of function in VHL or PHD2 or activating mutations of HIF-2α, all of which result in highly expressed HIF-2α protein and subsequently downstream genes to promote oncogenic progression (see Dahia, Nat Rev Cancer. 14:108-19, 2014). Furthermore, germline heterozygous mutations in genes encoding succinate dehydrogenase (SDH) subunits and the SDH complex assembly factor 2 protein (SDHAF2) have been described in patients with hereditary phaeochromocytoma and paraganglioma (PPGL). These mutations can lead to the accumulation of succinate, which in turn causes an inhibition of prolyl-hydroxylases that is essential in mediating ubiquitination/degradation of HIF proteins by VHL complex. Pituitary adenoma has been frequently found to be co-existing with PPGLs. Thus, inhibiting HIF-2α should be useful for treating both PPGLs and pituitary tumors. Succinate dehydrogenase subunits mutations have also been associated with gastrointestinal stromal tumors (GIST), thus supporting exploration of HIF-2α inhibitor for the treatment of GIST (see Janeway, et al. Proc. Natl Acad. Sci. USA 108: 314-318, 2011).

Loss-of-function mutations of fumarate hydratase (FH) predispose patients to the autosomal dominant syndrome of both cutaneous and uterine leiomyomatosis. It has been suggested that activation of HIF proteins contributes to FH-associated tumor development by activation of hypoxia pathways. (see O'Flaherty, et al. Hum Mol Genet. 19: 3844-3851, 2010 and Wei, et al. J Med Genet. 43:18-27, 2006). Furthermore, high expression of HIF-2α is found in leiomyosarcomas, a rare neoplasm of smooth-muscle origin (see Mayer, et al. Cancer Res. 68: 4719, 2008) Thus, inhibition of HIF-2α could be beneficial in treating both leiomyomas and leiomyosarcomas.

Retinal capillary hemangioblastomas can be the ocular manifestations of VHL diseases, which are caused by loss of tumor suppressor VHL. Upregulation of HIF-2α upon loss of VHL has been detected in retinal hemangioblastoma patients and is indicated to contribute to the aggressive course of retinal hemangioblastomas, resulting in the resistance to multiple anti-VEGF and radiation therapies (see Wang, et al. Graefes Arch. Clin. Exp. Ophthalmol. 252: 1319-1327, 2014). Moreover, uncontrolled blood vessel growth is a central pathological component of many human blindness disorders, including diabetic retinopathy, age-related macular degeneration, glaucoma, and retinopathy of prematurity. Neuronal cell death and vision loss observed in these diseases are often caused by aberrant, leaky vessels, results of pathological neovascularization (see Krock, et al. Genes Cancer. 2: 1117-1133, 2011). Given the causal role of HIFs in neovascularization, inhibitor of HIF-2α may have potential utility in treating various diseases of blindness. In fact, systemic reduction of HIF-2α expression with a hypomorphic Hif-2α allele caused marked decreases in retinal neovascularization that was accompanied by defects in EPO expression (see Morita, et al. EMBO J. 22: 1134-46, 2003).

In addition to a direct role in promoting the initiation, progression and metastasis of tumor cells (e.g. ccRCC), HIF-2α also indirectly contributes to tumorigenesis through augmenting the immunosuppressive effect of hypoxia within the tumor microenvironment. Expression of HIF-2α has been detected in cells of the myeloid lineage (see Talks K L, et dal. Am J Pathol. 2000; 157(2):411-421). For example, HIF-2α is shown to favor the polarization of macrophages to the immunosuppressive M2 phenotype and enhances migration and invasion of tumor-associated macrophages (see Imtiyaz H Z et al. J Clin Invest. 2010; 120(8):2699-2714). Thus, increased level of HIF-2α in tumor-associated macrophages (TAMs) is associated with high-grade human tumors and correlates with poor prognosis. Furthermore, HIF-2α can indirectly promote additional immunosuppressive pathways (e.g. adenosine and arginase etc.) by modulating the expression of key signaling regulators such as adenosine A2B/A2A receptors and arginase. These data support that HIF-2α is a potential therapeutic target for treating a broader range of inflammatory disorders and cancer either as a single agent or in combination with other therapeutic agents e.g., immunotherapies.

Due to the key roles of HIF-2α proteins in regulating physiological response to the fluctuation of oxygen levels, they have been causally associated with many hypoxia-related pathological processes in addition to cancer. One such disease is PAH, a debilitating and life-threatening disease with very poor prognosis. Recent studies demonstrated that HIF-2α contributes to the process of hypoxic pulmonary vascular remodeling, reduced plasticity of the vascular bed, and ultimately, debilitating PAH (see Andrew S., et al. Proc Natl Acad Sci USA. 2016 Aug. 2; 113(31): 8801-8806, Tang H, et al. Am J Physiol Lung Cell Mol Physiol. 2018 Feb. 1; 314(2):L256-L275.). These studies offered new understanding in the role of pulmonary endothelial HIF-2α in regulating the pulmonary vascular response to hypoxia, and offer an much needed new therapeutic strategy by targeting HIF-2α. Another example of hypoxia-related pathological processes is IBD, a chronic relapsing inflammatory disease of the intestine. It is found that intestinal inflammation and subsequently IBD arose when a dysregulated epithelial oxygen tension occurs and intensifies across epithelial villi in the intestine (see Shah Y. M., Molecular and Cellular Pediatrics, 2016 December; 3(1):1). HIF-2α activation contributes to IBD, while HIF-1α in intestinal epithelial cells is considered as a major protective factor in IBD (see Karhausen J, et al. J Clin Invest. 2004; 114(8): 1098-1106; Furuta G T, et al. J Exp Med. 2001; 193(9): 1027-1034). Mechanistically, HIF-2α activation not only leads to the upregulation of pro-inflammatory cytokines which promotes IBD directly, but also results in loss of intestine barrier integrity, thus indirectly contributes to the manifestation of IBD. (see Xue X, et al. Gastroenterology. 2013; 145(4):831-841; Glover L E, et al. Proc Natl Acad Sci USA. 2013; 110(49):19820-19825). Therefore, an HIF-2α inhibitor holds the promise of reverting the pro-inflammatory condition and increasing the intestinal barrier integrity, thus alleviate the symptoms of IBD.

HIF-2α inhibitor also represents a novel therapeutic approach in NASH, for which limited therapeutic options are available. A recent study showed that an intestine-specific disruption of HIF-2α led to a significant reduction of hepatic steatosis and obesity induced by high-fat-diet. Mechanistically, intestine HIF-2α positively regulates the gene encoding neuraminidase 3, thus regulates ceramide metabolism which contributes to the development of NASH (see Xie C, et al. Nat Med. 2017 November; 23(11):1298-1308.). Therefore, a HIF-2α inhibitor should have preventive and therapeutic effects on metabolic disorders, such as NASH.

Several connections between the level of HIF-2α and iron homeostasis have been identified (see Peyssonnaux C et al, Cell Cycle. 2008; 7(1):28-32). Multiple studies have demonstrated the important role of HIF-2α in iron load disorders. HIF-2α, not HIF-1α, has emerged as an important "local" regulator of intestinal iron status through its regulation of various genes essential in iron transport and absorption (see Mastrogiannaki M, et al. J Clin Invest. 2009; 119(5):1159-1166). Therefore, a small molecule inhibitor that targets HIF-2α holds promise of improving iron homeostasis in patients with iron disorders.

Accordingly, the present disclosure provides a method for treating or lessening the severity of a disease, condition, or disorder where activation or over activation of HIF-2α is implicated in the disease state. In another aspect, the present disclosure provides a method of treating renal cell carcinoma of a subject with Compound 1.

HIF-2α inhibitors also have therapeutic potentials for a broad range of non-cancer indications including but not limited to NASH, IBD, PAH, and iron overload.

Pharmaceutical Compositions

In general, Form A polymorph of Compound 1 will be administered in a therapeutically effective amount by any of the accepted modes of administration for agents that serve similar utilities. Therapeutically effective amounts of Form A polymorph of Compound 1 may range from about 200 mg/per day to about 1000 mg/per day, which can be administered in single or multiple doses. For oral administration, the compositions can be provided in the form of tablets containing about 50, 75, 100, 150, 200, 250, 300, 400, 500, 600, 750, 800, 900, and 1000 milligrams of the active ingredient. The actual amount of Form A polymorph of Compound 1 will depend upon numerous factors such as the severity of the disease to be treated, the age and relative health of the patient, the potency of the compound being utilized, the route and form of administration, and other factors.

In general, Form A polymorph of Compound 1 will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules, including enteric coated or delayed release tablets, pills or capsules are preferred) and the bioavailability of the drug substance.

The compositions are comprised of in general, Form A polymorph of Compound 1 in combination with at least one pharmaceutically acceptable excipient. Acceptable excipients are non-toxic, aid administration, and do not adversely affect the therapeutic benefit of Form A polymorph of Compound 1. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice flour, chalk, silica gel, magnesium stearate, sodium stearate, glycerol monostearate, sodium chloride, dried skim milk and the like. Liquid and semisolid excipients may be independently selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Form A polymorph of Compound 1 may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of Form A polymorph of Compound 1 which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of Form A polymorph of Compound 1 to allow for the preparation of highly concentrated solutions.

In addition to the formulations described previously, Form A polymorph of Compound 1 may also be formulated as a depot preparation. Such long-acting formulations may be administered by implantation (for example subcutaneously or intramuscularly) or by intramuscular injection. Thus, for example, Form A polymorph of Compound 1 may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise Form A polymorph of Compound 1 in a flavored basis such as sucrose and acacia or tragacanth.

Other suitable pharmaceutical excipients and their formulations are described in Remington's Pharmaceutical Sciences, edited by E. W. Martin (Mack Publishing Company, 20th ed., 2000).

The level of Form A polymorph of Compound 1 in a formulation can vary within the full range employed by those skilled in the art. Typically, the formulation will contain, on a weight percent (wt. %) basis, from about 0.01-99.99 wt. % of Form A polymorph of Compound 1 based on the total formulation, with the balance being one or more suitable pharmaceutical excipients. For example, the compound is present at a level of about 1-80 wt. %.

Combinations and Combination Therapies

Form A polymorph of Compound 1 may be used in combination with one or more other drugs in the treatment of diseases or conditions for which Form A polymorph of Compound 1 or the other drugs may have utility. Such other drug(s) may be administered, by a route and in an amount commonly used therefore, contemporaneously or sequentially with Form A polymorph of Compound 1. When Form A polymorph of Compound 1 is used contemporaneously with one or more other drugs, a pharmaceutical composition in unit dosage form containing such other drugs and Form A polymorph of Compound 1 is preferred. However, the combination therapy may also include therapies in which Form A polymorph of Compound 1 and one or more other drugs are administered on different overlapping schedules. It is also contemplated that when used in combination with one or more other active ingredients, Form A polymorph of Compound 1 and the other active ingredients may be used in lower doses than when each is used singly.

Accordingly, the pharmaceutical compositions of the present disclosure also include those that contain one or more other drugs, in addition to Form A polymorph of Compound 1.

The above combinations include combinations of Form A polymorph of Compound 1 not only with one other drug, but also with two or more other active drugs. Likewise, Form A polymorph of Compound 1 may be used in combination with other drugs that are used in the prevention, treatment, control, amelioration, or reduction of risk of the diseases or conditions for which Form A polymorph of Compound 1 is useful. Such other drugs may be administered, by a route and in an amount commonly used therefore, contemporaneously or sequentially with Form A polymorph of Compound 1. When Form A polymorph of Compound 1 is used contemporaneously with one or more other drugs, a pharmaceutical composition containing such other drugs in addition to Form A polymorph of Compound 1 can be used. Accordingly, the pharmaceutical compositions of the present disclosure also include those that also contain one or more other active ingredients, in addition to Form A polymorph of Compound 1. The weight ratio of Form A polymorph of Compound 1 to the second active ingredient may be varied and will depend upon the effective dose of each ingredient Generally, an effective dose of each will be used.

Where the subject in need is suffering from or at risk of suffering from cancer, the subject can be treated with Form A polymorph of Compound 1 in any combination with one or more other anti-cancer agents. In some embodiments, one or more of the anti-cancer agents are proapoptotic agents. Examples of anti-cancer agents include, but are not limited to, any of the following: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec™), geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel", which is a well-known anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Suitable anti-cancer agents also include inhibitors of kinases associated cell proliferative disorder. These kinases include but not limited to Aurora-A, BTK, CDK1, CDK2, CDK3, CDK4, CDK6, CDK5, CDK7, CDK8, CDK9, ephrin receptor kinases, CHK1, CHK2, SRC, Yes, Fyn, Lck, Fer, Fes, Syk, Itk, Bmx, GSK3, JNK, MEK, PAK1, PAK2, PAK3, PAK4, PDK1, PKA, PKC, RAF, Rsk and SGK. In particular, inhibitors of CDK4/6, including abemaciclib (Verzenio), palbociclib (Ibrance) and ribociclib (Kisqali), have the potential to be synergistic with HIF-2α inhibitors and reverse the resistance to HIF-2α inhibition; mitogen-activated protein kinase signaling, e.g., U0126, PD98059, PD184352, PD0325901, ARRY-142886, SB239063, SP600125, BAY 43-9006, wortmannin, or LY294002; Syk inhibitors; antibodies (e.g., rituxan); MET inhibitor such as foretinib, carbozantinib, or crizotinib; VEGFR inhibitor such as sunitinib, sorafenib, regorafinib, lenvatinib, vandetanib, carbozantinib, axitinib; EGFR inhibitor such as afatinib, brivanib, carbozatinib, erlotinib, gefitinib, neratinib, lapatinib; PI3K inhibitor such as XL147, XL765, BKM120 (buparlisib), GDC-0941, BYL719, IPI145, BAY80-6946. BEX235 (dactolisib), CAL101 (idelalisib), GSK2636771, TG100-115; MTOR inhibitor such as rapamycin (sirolimus), temsirolimus, everolimus, XL388, XL765, AZD2013, PF04691502, PKI-587, BEZ235, GDC0349; MEK inhibitor such as AZD6244, trametinib, PD184352, pimasertinib, GDC-0973, AZD8330; CSF1R inhibitors (PLX3397, LY3022855, etc.) and CSF1R antibodies (IMC-054, RG7155, etc); TGF beta receptor kinase inhibitor such as LY2157299; BTK inhibitor such as ibrutinib.

Other anti-cancer agents include proteasome inhibitor such as carfilzomib, MLN9708, delanzomib, or bortezomib; BET inhibitors such as INCB054329, OTX015, CPI-0610; LSD1 inhibitors such as GSK2979552, INCB059872; HDAC inhibitors such as panobinostat, vorinostat; DNA methyl transferase inhibitors such as azacytidine, decitabine), and other epigenetic modulator; SHP-2 inhibitor such as TNO155; Bcl2 inhibitor ABT-199, and other Bcl-2 family protein inhibitors; HIF-2α inhibitors such as PT2977 and PT2385; Beta catenin pathway inhibitors, notch pathway inhibitors and hedgehog pathway inhibitors; Antibodies or other therapeutic proteins against VEGF include bevacizumab and aflibercept.

Other anti-cancer agents/drugs that can be used in combination with the compounds of the invention include, but are not limited to, liver X receptor (LXR) modulators, including LXR agonists and LXR beta-selective agonists; aryl hydrocarbon receptor (AhR) inhibitors.

Other anti-cancer agents that can be employed in combination with Form A polymorph of Compound 1 include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or Ril2), interferon alfa-2a; interferon alfa-2b; interferon alfa-n1; interferon alfa-n3; interferon beta-1a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be employed in combination with Form A polymorph of Compound 1 include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; beta-clamycin B; betulinic acid; Bfgf inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; fmasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras famesyl protein transferase inhibitors; ras inhibitors; ras-GAP inhibitor; retelliptine demethylated; rhenium Re 186 etidronate; rhizoxin; ribozymes; R.sub.11 retinamide; rogletimide; rohitukine; romurtide; roquinimex; rubiginone Bi; ruboxyl; safingol; saintopin; SarCNU; sarcophytol A; sargramostim; Sdi 1 mimetics; semustine; senescence derived 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with Form A polymorph of Compound 1 include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., cytarabine), purine analogs (e.g., mercaptopurine, thioguanine, pentostatin).

Examples of natural products useful in combination with Form A polymorph of Compound 1 include but are not limited to vinca alkaloids (e.g., vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination with Form A polymorph of Compound 1 include, but are not limited to, nitrogen mustards (e.g., mechloroethamine, cyclophosphamide, chlorambucil, melphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), ortriazenes (decarbazine, etc.). Examples of antimetabolites include, but are not limited to folic acid analog (e.g., methotrexate), or pyrimidine analogs (e.g., fluorouracil, floxuridine, cytarabine), purine analogs (e.g., mercaptopurine, thioguanine, pentostatin.

Examples of hormones and antagonists useful in combination with Form A polymorph of Compound 1 include, but are not limited to, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Other anti-cancer agents that can be employed in combination with Form A polymorph of Compound 1 include: anti-cancer agents which act by arresting cells in the G2-M phases due to stabilized microtubules and include Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39·HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B. Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

One or more additional immune checkpoint inhibitors can be used in combination with Form A polymorph of Compound 1 for treatment of HIF-2α-associated diseases, disorders or conditions. Exemplary immune checkpoint inhibitors include inhibitors (smack molecules or biologics) against immune checkpoint molecules such as CD27, CD28, CD40, CD122, CD96, CD73, CD39, CD47, OX40, GITR, CSF1R, JAK, PI3K delta, PI3K gamma, TAM, arginase, CD137 (also known as 4-1BB), ICOS, A2AR, A2BR, SHP-2, B7-H3, B7-H4, BTLA, CTLA-4, LAG3, TIM3, VISTA, CD96, TIGIT, PD-1, PD-L1 and PD-L2. In some embodiments, the immune checkpoint molecule is a stimulatory checkpoint molecule selected from CD27, CD28, CD40, ICOS, OX40, GITR, CD137 and STING. In some embodiments, the immune checkpoint molecule is an inhibitory checkpoint molecule selected from B7-H3, B7-H4, BTLA, CTLA-4, IDO, TDO, Arginase, KIR, LAG3, PD-1, TIM3, CD96, TIGIT and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, PDR001, or AMP-224. In some embodiments, the anti-PD-1 monoclonal antibody is nivolumab, or pembrolizumab or PDR001. In some embodiments, the anti-PD1 antibody is pembrolizumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A (atezolizumab) or MEDI4736 (durvalumab).

In some embodiments, the inhibitor of an immune checkpoint molecule is an inhibitor of CTLA-4, e.g., an anti-CTLA-4 antibody. In some embodiments, the anti-CTLA-4 antibody is ipilimumab or tremelimumab. In some embodiments, the inhibitor of an immune checkpoint molecule is an inhibitor of LAG3, e.g., an anti-LAG3 antibody. In some embodiments, the anti-LAG3 antibody is BMS-986016 or LAG525. In some embodiments, the inhibitor of an immune checkpoint molecule is an inhibitor of GITR, e.g., an anti-GITR antibody. In some embodiments, the anti-GITR antibody is TRX518 or, MK-4166, INCAGN01876 or MK-1248. In some embodiments, the inhibitor of an immune checkpoint molecule is an inhibitor of OX40, e.g., an anti-OX40 antibody or OX40L fusion protein. In some embodiments, the anti-OX40 antibody is MEDI0562 or, INCAGN01949, GSK2831781, GSK-3174998, MOXR-0916, PF-04518600 or LAG525. In some embodiments, the OX40L fusion protein is MEDI6383.

Form A polymorph of Compound 1 can also be used to increase or enhance an immune response, including increasing the immune response to an antigen; to improve immunization, including increasing vaccine efficacy; and to increase inflammation. In some embodiments, the compounds of the invention can be sued to enhance the immune response to vaccines including, but not limited, Listeria vaccines, oncolytic viral vaccines, and cancer vaccines such as GVAX® (granulocyte-macrophage colony-stimulating factor (GM-CF) gene-transfected tumor cell vaccine). Anticancer vaccines include dendritic cells, synthetic peptides, DNA vaccines and recombinant viruses. Other immunemodulatory agents also include those that block immune cell migration such as antagonists to chemokine receptors, including CCR2 and CCR4; Sting agonists and Toll receptor agonists.

Other anti-cancer agents also include those that augment the immune system such as adjuvants or adoptive T cell transfer. Form A polymorph of Compound 1 may be effective in combination with CAR (Chimeric antigen receptor) T cell treatment as a booster for T cell activation.

EXAMPLES

The following preparations of Compound 1 are given to enable those skilled in the art to more clearly understand and to practice the present disclosure. They should not be considered as limiting the scope of the disclosure, but merely as being illustrative and representative thereof.

Example 1

Synthesis of diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile

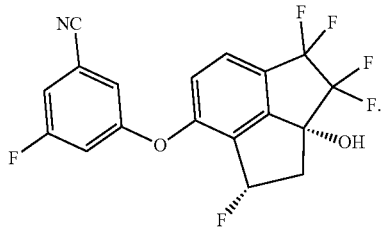

To a stirred solution of 3-fluoro-5-(((1R,2aR)-3,3,4,4-tetrafluoro-1,2a-dihydroxy-2,2a,3,4-tetrahydro-1H-cyclopenta[cd]inden-7-yl)oxy)benzonitrile (100.00 g, 260.91 mmol, 1.00 eq.) and DBU (79.44 g, 521.81 mmol, 2.00 eq.) in THF (2.2 L) was added a solution of pyridine-2-sulfonyl fluoride (50.46 g, 313.12 mmol, 1.20 eq.) in THF (400 mL) slowly at 20-25° C. over 2 h under nitrogen atmosphere. The resulting mixture was stirred further for 16 h at 20-25° C., and then quenched with 0.78 N aqueous NaOH (1.0 L). After stirring at 20-30° C. for 30 min., the layers were separated. The aqueous layer was extracted with MTBE. The combined organic layer was washed with 10% brine, and then concentrated to about a 350 mL solution. This solution was diluted with MTBE, washed with 0.5 N aqueous HCl, and then water. The organic layer was concentrated to about 200 mL (HPLC purity of 94.1 A %, and chiral purity was 97.2% ee), diluted with EtOAc, and then loaded onto a silica gel pad and the pad was rinsed with EtOAc/n-heptane=1/5 until no product eluted. The desired fractions were concentrated, and the solvent was swapped with MTBE to obtain a MTBE solution (about 350 mL).

Diethylamine (600 mL) was added, and the resulting solution was heated to 35-45° C., and n-heptane (400 mL) was added slowly at this temperature over 2 h. The resulting slurry was stirred at 35-45° C. for 1 h, and then solid crystalline seed of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile Form A polymorph (0.5 g) was added. After further stirring at 35-45° C. for 1 h, the slurry was cooled slowly to −5 to 5° C., and then n-heptane (2.0 L) was added slowly over 5 h. After further stirring at −5 to 5° C. for 6 h, the mixture was filtered, and the solid cake was washed with cold DEA/n-heptane (1:4) to give the title compound.

Example 2

Synthesis of crystalline Form A of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile

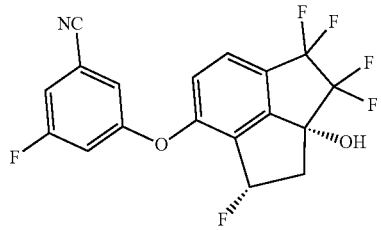 [SMILES: N#Cc1cc(F)cc(Oc2ccc3c4c2[C@@H](F)C[C@]4(O)C(F)(F)C3(F)F)c1]

3-Fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile:DEA solvate was vacuum dried at 65-70° C. for 20 h to obtain 53.2 g of the title compound. The HPLC purity of the title compound was 99.8 A % and chiral purity was 100.0% ee.). $^1$H NMR (400 MHz, CDCl$_3$) δ=7.71-7.67 (m, 1H), 7.29-7.26 (m, 2H), 7.25-7.09 (m, 2H), 6.60-5.80 (ddd, 1H), 2.87 (s, 1H), 2.91-2.57 (m, 2H).

To a stirred clear solution of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile (50.0 g) in IPA (150 mL) was added slowly n-heptane (100 mL) at 20-30° C. over 1 h, followed by seed crystal of the title compound (0.25 g of Form A polymorph of Compound 1), and the resulting slurry was stirred at 20-30° C. for 3 h. n-Heptane (150 mL) was added slowly over 4 h at 20-30° C., followed by additional n-heptane (950 mL) over 8 h. After further stirring at 20-30° C. for 3 h, the slurry was cooled slowly to −10-0° C. over 4 h, and then stirred at this temperature for 6 h. The mixture was filtered and the solid cake was rinsed with cold n-heptane. The solid was vacuum dried at 45-55° C. for 12 h to obtain the title product (46.73 g, 93.5% yield). The HPLC purity was 99.9 A % and chiral purity was 100.0% ee.

Alternate Method for Preparing Compound 1 from its DEA Solvate:

To a stirred mixture of Compound 1.DEA solvate (10.0 g) in EtOAc (150 mL) is added 0.5 M aqueous HCl (150 mL) at 20-30° C. The resulting mixture is stirred at this temperature for 30 min. The organic layer is separated, and then washed with water. The organic layer is concentrated and the residue is recrystallized from IPA/n-heptane to obtain the title Compound 1.

Example 3

Alternative Synthesis, Purification, and Polymorph Characterization of Compound 1

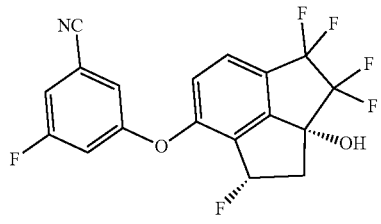 [SMILES: N#Cc1cc(F)cc(Oc2ccc3c4c2[C@@H](F)C[C@]4(O)C(F)(F)C3(F)F)c1]

Into a 3000 mL 3-necked round-bottom flask were added 3-fluoro-5-(((1R,2aR)-3,3,4,4-tetrafluoro-1,2a-dihydroxy-2,2a,3,4-tetrahydro-1H-cyclopenta[cd]inden-7-yl)oxy)benzonitrile (350 g, 0.762 mol, 1.0 equiv.) and DBU (232.1 g, 1.53 mol, 2.0 equiv.) in THF (3.5 L) at room temperature. To this solution was added dropwise a solution of pyridine-2-sulfonyl fluoride (159.7 g, 0.991 mmol, 1.3 equiv.) in THF (700 mL) at 10-15° C. The resulting mixture was stirred for 12 h at room temperature then diluted with water and EtOAc. The suspension was filtered through silica gel and the phases were separated. The aqueous layer was extracted with EtOAc and the combined organic layers were washed with water and brine, dried over anhydrous $Na_2SO_4$ and concentrated. The residue was purified by silica gel column chromatography (Petroleum ether/ethyl acetate=20/1 to 7/1) to give crude product (400 g) as off-white solid. The crude product was separated by SFC (column: DAICEL CHIRALPAK AS (250 mm*50 mm, 10 um) to give 250 g of crude product. To the crude product was added heptane (1.0 L) and the mixture was stirred at 40° C. for 2 hours. The mixture was filtered to give pure title product (230 g). The HPLC purity of the title compound was 98.7% and chiral purity was 99.1% ee. SFC condition: Column: Chiralpak AD-3 50×4.6 mm I.D., 3 m Mobile phase: Phase A, $CO_2$; Phase B, EtOH (0.05% DEA) Gradient elution: B in A from 5% to 40%; Flow rate: 3 mL/min Column Temp: 35° C.; Back Pressure: 100 Bar; $t_R$: 0.904 min.

Polymorph Characterization:

Compound 1 (15.5 mg) obtained from Example 3, was added into 0.4 mL of a mixture of n-pentanol/heptane (9:1) at 50° C. After stirring the mixture for 3 days, the solid was collected by filtration to give crystalline Form A polymorph. XRPD patterns were obtained with an X-ray diffractometer (Bruker D8 advance), at ambient temperature (23-25° C.) using an incident beam of Cu Kα (1.5418 Å), from a generator operating at 40 kV and 40 mA. The system was equipped with LynxEye detector. Samples of Compound 5 were scanned from 3 to 40° 2θ, at a step size 0.02° 2θ. Data was analyzed using DIFFRAC plus Evaluation Package Release 2010. The XRPD spectrum of crystalline Form A polymorph is shown in FIG. 3. The peak listing for XRPD spectrum, diffraction angles (2-Theta) reported in degrees was given in Table 1 below.

TABLE 1

Peak list of crystalline Compound 1 obtained from n-pentanol/heptane

| Angle (2-Theta °) | d value (Å) | Intensity % |
|---|---|---|
| 9.2 | 9.59 | 6.9 |
| 10.1 | 8.79 | 19.5 |
| 11.4 | 7.75 | 21.6 |
| 12.9 | 6.87 | 21.6 |
| 13.7 | 6.48 | 15.2 |
| 14.0 | 6.33 | 3.5 |
| 15.4 | 5.75 | 3.8 |
| 15.8 | 5.59 | 100 |
| 16.6 | 5.35 | 9.8 |
| 17.4 | 5.09 | 6.7 |
| 18.0 | 4.93 | 10.2 |
| 18.6 | 4.77 | 25.3 |
| 19.6 | 4.53 | 15.3 |
| 20.1 | 4.41 | 24.3 |
| 20.7 | 4.29 | 4 |
| 21.0 | 4.23 | 3.9 |
| 21.4 | 4.15 | 13.2 |
| 21.7 | 4.09 | 18.5 |
| 22.1 | 4.03 | 10.6 |
| 22.6 | 3.94 | 5.3 |
| 23.8 | 3.74 | 3 |
| 24.1 | 3.69 | 4.5 |
| 25.0 | 3.55 | 14.7 |
| 26.0 | 3.43 | 13.9 |
| 26.7 | 3.33 | 3.4 |
| 27.2 | 3.28 | 6.4 |
| 27.6 | 3.23 | 4.4 |
| 27.8 | 3.20 | 3.8 |
| 28.2 | 3.16 | 7.3 |
| 29.0 | 3.07 | 6.2 |
| 29.6 | 3.02 | 9.3 |
| 30.1 | 2.97 | 4.4 |
| 30.6 | 2.92 | 3 |
| 31.0 | 2.88 | 2.9 |
| 31.7 | 2.82 | 3.5 |
| 31.9 | 2.80 | 4 |
| 32.4 | 2.76 | 5.1 |
| 33.6 | 2.66 | 5.4 |
| 34.2 | 2.62 | 3.3 |
| 34.6 | 2.59 | 4.3 |
| 35.4 | 2.53 | 3.2 |
| 35.8 | 2.50 | 3.3 |

Crystallization of Compound 1 under following conditions also gave Form A polymorph.

Method A

Compound 1 (15 mg/m) was dissolved in MOH, IPA, MTBE, EtOAc, IPAc, or toluene and the solutions were allowed to evaporate at room temperature to give Compound 1 as a crystalline solid. XRPD analysis showed the crystalline solid was Form A polymorph.

Method B

Compound 1 (~10 mg) was added into 0.5 ml, of anti-solvent at 50° C. and then solvent was added to dissolve solid as shown in Table 3 below. The mixture was filtered and the solution was slowly cooled to room temperature and stirred at room temperature for one day. The crystals were filtered and XRPD analysis was performed.

TABLE 3

| Anti-solvent | Solvent | Crystal form |
|---|---|---|
| water | EtOH | Form A |
| water | IPA | Form A |
| Heptane | EtOH | Form A |
| Heptane | IPA | Form A |
| Heptane | toluene | Form A |

Method C

Compound 1 was dissolved in solvent, and anti-solvent was added with stirring at room temperature, 50° C., or ice bath as shown in Table 4 below. The crystalline solid was filtered and characterized by XRPD.

TABLE 4

| Amount (mg) | Solvent | Anti-solvent | Crystal Form |
|---|---|---|---|
| 21.18 | Heptane-EtOAc (3:2), 0.4 mL | Heptane, 1 mL | Form A |
| 11.20 | Toluene, 0.2 mL | Heptane, 0.3 mL | Form A |
| 10.45 | Acetone, 0.05 mL | Water, 0.25 mL | Form A |

TABLE 4-continued

| Amount (mg) | Solvent | Anti-solvent | Crystal Form |
|---|---|---|---|
| 10.29 | ACN, 0.05 mL | Water, 0.8 mL | Form A |
| 10.35 | 1,4-dioxane, 0.1 mL | Water, 0.3 mL | Form A |
| 10.52 | EtOH, 0.05 mL | Water, 0.1 mL | Form A |
| 10.37 | IPA, 0.15 mL | Water, 0.3 mL | Form A |
| 10.21 | MeOH, 0.05 mL | Water, 0.1 mL | Form A |
| 10.06 | EtOH, 0.05 | Heptane, 1 mL | Form A |

Method D

Compound 1 (~10 mg) was dissolved in solvent and then the resulting solution was added into 0.5 mL of anti-solvent. The mixture was kept stirring at room temperature for one day and the crystalline solid was analyzed by XRPD. The results were shown in Table 5 below.

TABLE 5

| Amount (mg) | Solvent | Anti-solvent | Crystal Form |
|---|---|---|---|
| 10.03 | Toluene, 0.15 mL | Heptane, 0.5 mL | Form A |
| 9.88 | Acetone, 0.05 mL | Water, 0.5 mL | Form A |
| 9.91 | 1,4-dioxane, 0.05 mL | Water, 0.5 mL | Form A |
| 9.92 | ACN, 0.05 mL | Water, 0.5 mL | Form A |
| 9.97 | EtOH, 0.05 mL | Water, 0.5 mL | Form A |
| 10.34 | IPA, 0.15 mL | Water, 0.5 mL | Form A |

Example 4

Preparation of DEA Solvate of Compound 1 and Compound 1

Synthesis and Polymorph Characterization of DEA Solvate of Compound 1:

To a stirred solution of crude 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile (25.1 g) in MTBE (75 mL) was added DEA (150 mL) at 35-45° C., followed by n-heptane (100 mL) slowly, and solid crystalline seed of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile Form A polymorph was added. The resulting slurry was stirred at 35-45° C. for 1 h, cooled slowly to −5 to 5° C., and then stirred at this temperature for 6 h. n-Heptane (500 mL) was added slowly over 4 h at −5 to 5° C. After stirring at −5 to 5° C. for 4 h, the slurry was filtered, washed with cold solution of DEA/Heptane=1V/4V and XPRD and NMR was done on the DEA solvate of Compound 1.

XRPD patterns of DEA solvate of Compound 1 were obtained with an X-ray diffractometer (Bruker D8 advance), at ambient temperature (about 23-25° C.) using an incident beam of Cu Kα (1.5406 Å), from a generator operating at 40 kV and 40 mA. The system was equipped with LynxEye detector. Samples of diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)-benzonitrile were scanned from 3 to 40° 2θ, at a step size 0.02° 2θ. Data was analyzed using DIFFRAC plus Evaluation Package Release 2010. The XRPD spectrum of crystalline Form B polymorph is shown in FIG. 1. The peak listing for XRPD spectrum, diffraction angles (2-Theta) reported in degrees was given in Table 2 below.

TABLE 2

| Angle (2-Theta °) | d value (Å) | Intensity % |
|---|---|---|
| 7.5 | 11.71 | 0.6 |
| 8.4 | 10.57 | 28.0 |
| 9.5 | 9.35 | 10.3 |
| 10.6 | 8.35 | 0.2 |
| 11.1 | 7.98 | 0.5 |
| 11.7 | 7.55 | 12.1 |
| 12.2 | 7.27 | 1.3 |
| 12.5 | 7.10 | 1.3 |
| 13.1 | 6.77 | 0.5 |
| 13.4 | 6.61 | 0.6 |
| 13.8 | 6.41 | 100.0 |
| 14.6 | 6.06 | 7.5 |
| 15.4 | 5.74 | 1.8 |
| 15.8 | 5.61 | 0.6 |
| 16.7 | 5.29 | 0.5 |
| 17.1 | 5.19 | 2.1 |
| 17.7 | 5.00 | 1.9 |
| 19.0 | 4.68 | 8.9 |
| 19.2 | 4.61 | 0.7 |
| 19.5 | 4.54 | 1.2 |
| 19.8 | 4.47 | 0.6 |
| 20.1 | 4.41 | 1.6 |
| 20.6 | 4.30 | 2.0 |
| 21.3 | 4.17 | 46.2 |
| 21.8 | 4.08 | 0.8 |
| 22.3 | 3.99 | 2.8 |
| 22.6 | 3.94 | 6.0 |
| 23.1 | 3.85 | 1.1 |
| 23.3 | 3.82 | 5.5 |
| 23.5 | 3.78 | 16.0 |
| 24.7 | 3.60 | 7.9 |
| 25.2 | 3.53 | 6.3 |
| 25.6 | 3.48 | 3.0 |
| 26.3 | 3.39 | 0.9 |
| 26.7 | 3.33 | 0.3 |
| 27.2 | 3.27 | 0.4 |
| 27.6 | 3.23 | 1.2 |
| 27.8 | 3.21 | 1.6 |
| 28.2 | 3.16 | 3.8 |
| 28.6 | 3.12 | 2.3 |
| 29.5 | 3.03 | 5.8 |
| 29.6 | 3.02 | 3.8 |
| 30.0 | 2.98 | 3.0 |
| 30.4 | 2.94 | 0.6 |
| 31.1 | 2.87 | 4.4 |
| 31.9 | 2.81 | 0.5 |
| 32.4 | 2.76 | 0.5 |
| 33.0 | 2.72 | 2.7 |
| 33.5 | 2.68 | 0.4 |
| 34.3 | 2.61 | 0.4 |
| 34.9 | 2.57 | 0.9 |
| 35.3 | 2.54 | 0.9 |
| 35.6 | 2.52 | 0.8 |
| 36.4 | 2.46 | 5.5 |
| 36.8 | 2.44 | 0.8 |
| 37.8 | 2.38 | 1.0 |
| 38.3 | 2.35 | 1.3 |
| 39.2 | 2.30 | 0.3 |
| 39.3 | 2.29 | 0.5 |
| 39.6 | 2.27 | 0.6 |

Synthesis of Compound 1

A solution of crude 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile (26.3 g) in DCM (50 mL) was concentrated to dryness. To the residue was charged DCM (38 mL) and the resulting solution was heated to 35-40° C., followed by the addition of DEA (114 mL). After stirring at 35-40° C. for 10 min, n-heptane (190 mL) was added slowly. The resulting mixture was stirred at 35-40° C. for 30 min, and solid crystalline seed of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile Form A polymorph was added. The slurry was stirred at 35-40° C. for 3 h, n-heptane (266 mL) then was added slowly over 8 h. The slurry was cooled slowly to 0° C., and then stirred at this temperature for 5.5 h. The slurry was filtered, washed with cold solution of DEA/Heptane=1V/4V. The solid was dried at 65° C. under vacuum to obtain the title compound (14.7 g). XRPD measurement was taken under conditions described in Example 4.

Example 5

Alternative Deoxyfluorinating Reaction Conditions for Syntheses of Compound 1

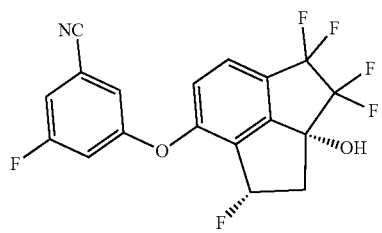 [SMILES: N#Cc1cc(F)cc(Oc2ccc3c4c2[C@@H](F)C[C@]4(O)C(F)(F)C3(F)F)c1]

Method A:

To a stirred solution of 3-fluoro-5-(((1R,2aR)-3,3,4,4-tetrafluoro-1,2a-dihydroxy-2,2a,3,4-tetrahydro-1H-cyclopenta[cd]inden-7-yl)oxy)benzonitrile (100.0 g, 260.91 mmol, 1.00 eq.) in MTBE (2.5 L) was added bis(2-methoxyethyl)aminosulfur trifluoride (BAST, 83.7 g, 378.32 mmol, 1.45 eq.) slowly over 2 h at −80 to −70° C. under nitrogen atmosphere. After stirring for an additional 2.5 h at −80 to −70° C., the reaction mixture was quenched with methanol (3344 mg, 104.37 mmol, 0.40 eq.) at −80 to −70° C. The resulting mixture was warmed to 0-10° C. and then quenched with 10% aqueous $K_2CO_3$ (1 L). The organic layer was separated, washed with water (1 L) and then concentrated.

The residue was purified with a silica gel pad (100 g silica gel), eluted with MTBE/n-heptane=1/2, to give the crude product. The crude was crystallized in MTBE/DEA/n-heptane=2V/6V/24V to give diethylamine solvate of Compound 1. The diethylamine solvate of Compound 1 was vacuum dried at 70° C. to give the Compound 1 as crystalline Form A polymorph (75.8 g, 75.4% yield). The purity of Compound 1 was 99.9% and the e.e was 99.9%.

Method B:

To a stirred solution of 3-fluoro-5-(((1R,2aR)-3,3,4,4-tetrafluoro-1,2a-dihydroxy-2,2a,3,4-tetrahydro-1H-cyclopenta[cd]inden-7-yl)oxy)benzonitrile (100.0 g, 0.26 mol, 1.00 eq.) in 2-MeTHF (2.5 L) was added $Et_3N·3HF$ (21.0 g, 0.13 mol, 0.50 eq.), followed by 2-tert-butyl-1,1,3,3-tetramethylguanidine (BTMG, 111.0 g, 0.65 mol, 2.50 eq.) at −20° C. under nitrogen. To the stirred resulting mixture, a solution of perfluorobutanesulfonyl fluoride (PBSF, 118.0 g, 0.39 mol, 1.50 eq.) in 2-MeTHF (500 mL) was added slowly over 1 h at −20° C. After stirring for 2 h, the mixture was quenched with deionized water (1 L).

The separated organic layer was washed with aqueous HCl, water, aqueous NaOH and then 10% brine. The separated organic layer was concentrated, dissolved in 2-MeTHF (750 mL), and concentrated again. The residue was dissolved in MeOH (1.5 L) and decolorized with activated charcoal (30 g) at 50° C. for 4 h. The resulting mixture was filtered to give a yellow filtrate. The filtrate was concentrated, and the residue was dissolved in 2-MeTHF (1.5 L) and then concentrated again. The residue was mixed with MTBE (2 L) at 40° C., stirred for 30 min, cooled to 20° C. and then filtered to remove the solid. The filtrate was concentrated and the residue was crystallized from MTBE/DEA/n-heptane=3V/6V/24V to give diethylamine solvate of Compound 1 (85 g) as beige solid.

Diethylamine solvate of Compound 1 (42.5 g) was mixed with MTBE (850 mL) and the resulting mixture was washed with 0.1 M aqueous HC, followed by 10% brine. The organic layer was separated and concentrated. The residue was dissolved in IPA (640 mL), and then decolorized with activated charcoal (8.5 g) at 40° C. for 4 h. The mixture was filtered, and the filtrate was concentrated. The residue was recrystallized from IPA/n-heptane=3V/24V and then vacuum dried to obtain the Compound 1 as crystalline Form A polymorph (30.5 g, 61.0% yield) as white solid. The purity was of Compound 1 was 100.0%.

Alternate reaction conditions explored for Method B above and the results obtained therefrom are disclosed in Tables 3 to 6 below. In the tables below, 3-fluoro-5-(((1R,2aR)-3,3,4,4-tetrafluoro-1,2a-dihydroxy-2,2a,3,4-tetrahydro-1H-cyclopenta[cd]inden-7-yl)oxy)-benzonitrile is referred to as SM and Compound is referred to as Product.

TABLE 3A

Deoxyfluorination with 1.2 eq. PBSF in THF from 0° C. to room temperature with various bases:

| Base (2.0 eq.) | Additive (1.2 eq.) | Reaction time (h) | IPC (A %) by HPLC SM | Product | Assay Yield (%) by HPLC |
|---|---|---|---|---|---|
| EtN | Et₃N·3HF | 18 | 41.7 | 39.5 | 37 |
| DBU | Et₃N·3HF | 18 | 33.8 | 48.3 | 44 |
| DBU | None | 20 | 14.8 | 39.2 | 43 |
| MTBD | Et₃N·3HF | 18 | 37.6 | 49.3 | 46 |
| BTMG | Et₃N·3HF | 18 | 48.4 | 41.5 | 38 |
| BTPP | Et₃N·3HF | 18 | 60.4 | 36.0 | 37 |

TABLE 4A

Deoxyfluorination reaction with 1.5 eq PBSF and Et₃N·3HF (0.5 eq) in THF from 0° C. to room temperature:

| Base (2.0 eq) | Additive (0.5 eq.) | Reaction time (h) | IPC (A%) by HPLC SM | Product | Assay by HPLC Yield (%) |
|---|---|---|---|---|---|
| BTPP | Et₃N·3HF | 18 | 2.9 | 89.4 | 81 |
| DBU | Et₃N·3HF | 18 | 1.6 | 80.9 | 65 |
| TMG | Et₃N·3HF | 18 | 2.2 | 73.0 | 57 |
| MTBD | Et₃N·3HF | 18 | 14.2 | 68.4 | |
| BTMG | Et₃N·3HF | 18 | 3.5 | 85.0 | |

TABLE 5A

Deoxyfluorination reaction with PBSF, BTMG and Et₃N•3HF at −10° C. to room temperature in various solvents:

| Solvent | PBSF (eq) | Et₃N•3HF (eq) | Time (h) | IPC (A %) by HPLC SM | IPC (A %) by HPLC Product | Assay Yield (%) by HPLC |
|---|---|---|---|---|---|---|
| Toluene | 1.5 | 0.25 | 21 | 1.9 | 74.9 | 66 |
| EtOAc | 1.5 | 0.25 | 21 | 1.8 | 77.6 | 61 |
| MeTHF | 1.5 | 0.25 | 21 | 1.2 | 78.9 | 69 |

TABLE 6A

Deoxyfluorination reaction with PBSF, BTMG and Et₃N•3HF in 2-MeTHF at −20° C.:

| Scale | Reaction condition | Time | IPC (A%) by HPLC SM | IPC (A%) by HPLC Product | Assay Yield (%) by HPLC |
|---|---|---|---|---|---|
| 3 g | 2.5 eq. BTMG 0.5 eq. Et₃N•3HF 1.5 eq. PBSF | 1 h | 2 | 91 | 90 |
| 15 g | 2.5 eq. BTMG 0.5 eq. Et₃N•3HF 1.5 eq. PBSF | 1 h | 2 | 91 | 88 |

Formulation Examples

The following are representative pharmaceutical formulations containing a compound of the present disclosure.

Tablet Formulation

The following ingredients are mixed intimately and pressed into single scored tablets.

| Ingredient | Quantity per tablet (mg) |
|---|---|
| compound of this disclosure | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule (mg) |
|---|---|
| compound of this disclosure | 200 |
| lactose spray dried | 148 |
| magnesium stearate | 2 |

Injectable Formulation

Compound of the disclosure (e.g., a compound of Formula I) in 2% HPMC, 1% Tween 80 in DI water, q.s. to at least 20 mg/mL Inhalation Composition To prepare a pharmaceutical composition for inhalation delivery, 20 mg of a compound disclosed herein is mixed with 50 mg of anhydrous citric acid and 100 mL of 0.9% sodium chloride solution. The mixture is incorporated into an inhalation delivery unit, such as a nebulizer, which is suitable for inhalation administration.

Topical Gel Composition

To prepare a pharmaceutical topical gel composition, 100 mg of a compound disclosed herein is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Ophthalmic Solution Composition

To prepare a pharmaceutical ophthalmic solution composition, 100 mg of a compound disclosed herein is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Nasal Spray Solution

To prepare a pharmaceutical nasal spray solution, 10 g of a compound disclosed herein is mixed with 30 mL of a 0.05M phosphate buffer solution (pH 4.4). The solution is placed in a nasal administrator designed to deliver 100 ul of spray for each application.

What is claimed:

1. An amine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile, wherein the amine is:
   (i) $NHR^1R^2$ where (1) $R^1$ is hydrogen and $R^2$ is $C_2$-$C_{12}$ alkyl, $C_2$-$C_6$ alkenyl, $C_2$-$C_6$ alkynyl, $C_3$-$C_7$ cycloalkyl, or $C_3$-$C_7$ cycloalkyl-$C_{1-6}$ alkyl; (2) $R^1$ is $C_1$-$C_6$ alkyl, $C_2$-$C_6$ alkenyl, $C_2$-$C_6$ alkynyl, $C_3$-$C_7$ cycloalkyl, or $C_3$-$C_7$ cycloalkyl-$C_{1-6}$ alkyl and $R^2$ is $C_1$-$C_6$ alkyl, $C_2$-$C_6$ alkenyl, $C_2$-$C_6$ alkynyl, $C_3$-$C_7$ cycloalkyl, or $C_3$-$C_7$ cycloalkyl-$C_{1-6}$ alkyl; or (3) $R^1$ and $R^2$ together with the nitrogen atom to which they are attached form cyclylamine; or
   (ii) $R^3R^4N$—$(CH_2)_n$—$NR^5R^6$ where n is an integer selected from 1 to 6 and $R^3$, $R^4$, $R^5$, and $R^6$ are independently H, $C_1$-$C_6$ alkyl, or $C_3$-$C_7$ cycloalkyl.

2. The amine solvate of claim 1, wherein the amine is $NHR^1R^2$.

3. The amine solvate of claim 2, wherein $R^1$ is $C_1$-$C_6$ alkyl and $R^2$ is $C_1$-$C_6$ alkyl.

4. The amine solvate of claim 3, wherein the amine is diethylamine and the stoichiometric ratio of the diethylamine to 3-fluoro-5-(((1S,2aR)-1,3,3,4,4-pentafluoro-2a-hydroxy-2,2a,3,4-tetrahydro-1H-cyclopenta[cd]-inden-7-yl)oxy)benzonitrile in the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)-benzonitrile is about 1:1 or is 1:1.

5. The amine solvate of claim 3, wherein the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile is a solid.

6. A crystalline form of a diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile, designated as Form B polymorph, having an X-ray powder diffraction pattern comprising peaks at angular positions 13.8 and 21.3, wherein the angular positions may vary by +/−0.2° 2θ as measured by X-ray powder diffraction at ambient temperature using (Cu Kα) an X-ray wavelength of 1.5406 Å.

7. The crystalline Form B of claim 6, wherein the Form B X-ray powder diffraction pattern further comprises a peak at angular position 8.4, wherein the angular position may vary by ±0.2° 2θ.

8. The crystalline Form B of claim 6, wherein the Form B X-ray powder diffraction pattern further comprises peaks at angular positions 8.4 and 23.5, wherein the angular positions may vary by ±0.2° 2θ.

9. A process of preparing an amine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile)-benzonitrile, wherein the amine is:
  (i) NHR$^1$R$^2$ where (1) R$^1$ is hydrogen and R$^2$ is C$_2$-C$_{12}$ alkyl, C$_2$-C$_6$ alkenyl, C$_2$-C$_6$ alkynyl, C$_3$-C$_7$ cycloalkyl, or C$_3$-C$_7$ cycloalkyl-C$_{1-6}$ alkyl; (2) R$^1$ is C$_1$-C$_6$ alkyl, C$_2$-C$_6$ alkenyl, C$_2$-C$_6$ alkynyl, C$_3$-C$_7$ cycloalkyl, or C$_3$-C$_7$ cycloalkyl-C$_{1-6}$ alkyl and R$^2$ is C$_1$-C$_6$ alkyl, C$_2$-C$_6$ alkenyl, C$_2$-C$_6$ alkynyl, C$_3$-C$_7$ cycloalkyl, or C$_3$-C$_7$ cycloalkyl-C$_{1-6}$ alkyl; or (3) R$^1$ and R$^2$ together with the nitrogen atom to which they are attached form cyclylamine; or
  (ii) R$^3$R$^4$N—(CH$_2$)$_n$—NR$^5$R$^6$ where n is an integer selected from 1 to 6 and R$^3$, R$^4$, R$^5$, and R$^6$ are independently H, C$_1$-C$_6$ alkyl or C$_3$-C$_7$ cycloalkyl, comprising:
  (a1) contacting 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile with the amine NHR$^1$R$^2$ or R$^3$R$^4$—N—(CH$_2$)$_n$—R$^5$R$^6$ where R$^1$ and R$^2$ are as defined in (i), and R$^3$, R$^4$, R$^5$, R$^6$, and n are as defined in (ii), in the presence or absence of one or more suitable organic solvents to provide a mixture containing the amine solvate;
  (b1) optionally adding (i) one or more anti-solvent and/or (ii) a solid crystalline seed of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile, or a solid crystalline seed of the amine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile, or a combination thereof, to the mixture of Step (a1) to precipitate the amine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile; and
  (c1) isolating the precipitate of Step (b1) to obtain a solid amine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile.

10. The process of claim 9, wherein 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile is contacted with the amine by adding 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile to the amine or by adding the amine to a mixture of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile and one or more suitable organic solvents in Step (a1).

11. The process of claim 10, wherein the amine is diethylamine.

12. The process of claim 11, wherein the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile is a crystalline solid.

13. A process of preparing crystalline Form B polymorph of a diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile having an X-ray powder diffraction pattern comprising peaks at angular positions 13.8 and 21.3, wherein the angular positions may vary by +/−0.2° 2θ as measured by X-ray powder diffraction at ambient temperature using (Cu Kα) an X-ray wavelength of 1.5406 Å, comprising:
  (a2) contacting 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile with diethylamine, in the presence or absence of one or more suitable organic solvents to provide a mixture containing diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile;
  (b2) adding (i) one or more anti-solvent and/or (ii) a crystalline seed of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile, or a solid crystalline seed of the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile, or a combination thereof, to the mixture of Step (a2) to precipitate the crystalline Form B polymorph of the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile; and
  (c2) isolating the crystalline Form B polymorph of the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile.

14. The process of claim 13, wherein the diethylamine is added to a mixture of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile and one or more suitable organic solvents to provide the mixture of Step (a2).

15. The process of claim 14, wherein the one or more anti-solvents added to the mixture of Step (a2) to precipitate crystalline Form B polymorph of the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile is n-heptane.

16. A solid composition comprising a diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile and 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile, wherein the % weight ratio of the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile to 3-fluoro-5-(((1S,2aR)-1,3,3,4,4-pentafluoro-2a-hydroxy-2,2a,3,4-tetrahydro- 1H-cyclopenta[cd]inden-7-yl)oxy)benzonitrile in the composition is from about 1:9 to about 1:0.001.

17. The amine solvate of claim 3, wherein the amine is diethylamine.

18. The amine solvate of claim 3, wherein the amine is N-methylethylamine, N-methyl-n-propylamine, N-methyl-isopropylamine, N-ethyl-n-propylamine, N-ethyl-isopropylamine, N-methylbutylamine, N-methyl-2-butylamine, N-tert-butyl-methyl-amine, N-methylpentyl-1-amine, N-methyl-2-pentylamine, N-methyl-3-pentylamine, N,3-dimethylbutane-2-amine, N,2-dimethylbutane-2-amine, N,3-dimethylbutane-2-amine, N-ethyl-1-butylamine, N-ethyl-2-butylamine, N-ethyl-2-methyl-2-propylamine, N-ethyl-2-methylpropylamine, di-n-propylamine, di-isopropylamine, or N-isopropylpropylamine.

19. The crystalline Form B of claim 6, wherein the Form B X-ray powder diffraction pattern further comprises peaks at angular positions 8.4, 23.5, and 11.7, wherein the angular positions may vary by ±0.2° 2θ.

20. The crystalline Form B of claim 6, wherein the Form B X-ray powder diffraction pattern further comprises peaks at angular positions 8.4, 23.5, 11.7, and 9.5, wherein the angular positions may vary by ±0.2° 2θ.

21. The process of claim 9, further comprising converting the amine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile from any one of Steps (a1) to (c1) to 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile.

22. The process of claim 10, wherein 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile is contacted with the amine by adding the amine to a mixture of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile and one or more suitable organic solvents in Step (a1).

23. The process of claim 22, wherein the amine is the amine is $NHR^1R^2$ wherein $R^1$ is $C_1$-$C_6$ alkyl and $R^2$ is $C_1$-$C_6$ alkyl.

24. The process of claim 23, wherein the amine is diethylamine.

25. The process of claim 24, wherein the molar ratio of diethylamine to 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile in the mixture of Step (a1) is from 1:1 to about 10:1.

26. The process of claim 25, comprising adding (i) one or more anti-solvent and/or (ii) a solid crystalline seed of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile, or a solid crystalline seed of the amine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile, or a combination thereof, to the mixture of Step (a1) to precipitate the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile.

27. The process of claim 14, wherein the one or more suitable organic solvents of Step (a2) is methyl tert-butyl ether.

28. The process of claim 14, wherein one or more anti-solvent and/or (ii) a crystalline seed of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile, or a solid crystalline seed of the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile, or a combination thereof, are added to the mixture of Step (a2) to precipitate crystalline Form B polymorph of the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile wherein the one or more anti-solvent is n-hexane.

29. The process of claim 27, wherein one or more anti-solvent and/or (ii) a crystalline seed of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile, or a solid crystalline seed of the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile, or a combination thereof, are added to the mixture of Step (a2) to precipitate crystalline Form B polymorph of the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile wherein the one or more anti-solvent is n-hexane and the molar ratio of diethylamine to 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile in the mixture of Step (a2) is from 1:1 to about 10:1.

30. The process of claim 28, wherein the Form B X-ray powder diffraction pattern further comprises peaks at angular positions 8.4, 23.5, and 11.7, wherein the angular positions may vary by ±0.2° 2θ.

31. The process of claim 28, wherein the Form B X-ray powder diffraction pattern further comprises peaks at angular positions 8.4, 23.5, 11.7, and 9.5, wherein the angular positions may vary by ±0.2° 2θ.

32. The process of claim 30, further comprising isolating and converting the crystalline Form B polymorph of the diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile from Step (c2) to 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile.

33. The solid composition of claim 16, wherein the % weight ratio of diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile to 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile is about 1 to 0.1.

34. The solid composition of claim 16, wherein the % weight ratio diethylamine solvate of 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile to 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile is about 1 to 0.02.

* * * * *